US010695371B2

(12) United States Patent
Peng et al.

(10) Patent No.: US 10,695,371 B2
(45) Date of Patent: Jun. 30, 2020

(54) MODIFICATION OF EXTRACORPOREAL PHOTOPHERISIS TECHNOLOGY WITH PORPHYRIN PRECURSORS

(71) Applicant: Oslo Universitetssykehus HF, Oslo (NO)

(72) Inventors: Qian Peng, Oslo (NO); Trond Warloe, Oslo (NO); Jahn M. Nesland, Asker (NO); Eidi Christensen, Trondheim (NO); Odrun Arna Gederaas, Trondheim (NO); Toril Holien, Trondheim (NO)

(73) Assignee: Oslo Universitetssykehus HF, Oslo (NO)

( * ) Notice: Subject to any disclaimer, the term of this patent is extended or adjusted under 35 U.S.C. 154(b) by 0 days.

(21) Appl. No.: 15/306,442

(22) PCT Filed: Apr. 24, 2015

(86) PCT No.: PCT/EP2015/058986
§ 371 (c)(1),
(2) Date: Oct. 24, 2016

(87) PCT Pub. No.: WO2015/162279
PCT Pub. Date: Oct. 29, 2015

(65) Prior Publication Data
US 2017/0042938 A1    Feb. 16, 2017

(30) Foreign Application Priority Data

Apr. 24, 2014    (GB) .................................. 1407296.1

(51) Int. Cl.
| A61N 5/06 | (2006.01) |
| A61K 41/00 | (2020.01) |
| A61K 35/14 | (2015.01) |
| A61K 31/22 | (2006.01) |
| A61K 31/197 | (2006.01) |

(52) U.S. Cl.
CPC ............ *A61K 35/14* (2013.01); *A61K 31/197* (2013.01); *A61K 31/22* (2013.01); *A61K 41/0061* (2013.01); *A61K 41/0066* (2013.01)

(58) Field of Classification Search
None
See application file for complete search history.

(56) References Cited

U.S. PATENT DOCUMENTS

| 5,030,200 A | 7/1991 | Millard et al. | |
| 6,219,584 B1 * | 4/2001 | Lee ..................... | A61M 1/3681 436/519 |

FOREIGN PATENT DOCUMENTS

| EP | 0 196 515 A1 | 10/1986 |
| FR | 2 696 756 A1 | 4/1994 |
| JP | 2005-132766 | 5/2005 |
| JP | 2011-518781 | 6/2011 |
| WO | WO 95/19705 A1 | 7/1995 |
| WO | WO 2005/004862 A2 | 1/2005 |
| WO | WO 2009/124189 | 10/2009 |

OTHER PUBLICATIONS

Wachowska et al. Molecules , 2011, 16, 4140-4164) (Year: 2011).*
Hosseini et al. Proceedings of SPIE (7161), 716131; https://www.spiedigitallibrary.org/conference-proceedings-of-spie/7161/1/Photobleaching-behavior-of-protoporphyrin-IX-during-5-aminolevulinic-acid-marked/10. (Year: 2009).*
Communication pursuant to Article 94(3) EPC including First Examination Report issued by the European Patent Office dated Sep. 7, 2017 in connection with related European Application No. EP 15 718 489.6.
Schwartz, et al., "Photopheresis in HIV-1 infected patitents (Pt) using benzoporphyrin derivative (BPD-MA) induces apoptosis in CD4 cells, increases cytolytic T-cell activity, intracellular expression of chemokines, and decreases HIV infectivity and viral load", Blood, 2006, vol. 108, No. 11, abstract.
Stewart, et al., "Photopheresis in HIV-1 infected patients using benzoporphyrin derivative (BPD-MA) and light induces apoptosis in CD4 cells and decreases HIV infectivity", Blood, 2001, vol. 98, No. 11, abstract.
Sanford, et al., "Extracorporeal photopheresis: Clinical use so far", Journal of Clinical Apheresis, 2012, vol. 27, No. 3, pp. 126-131.
H. Peter Van Iperen, et al., "Singlet oxygen producing photosensitizers in photophoresis", Journal of Photochemistry and Photobiology B: Biology, Apr. 1, 1997, vol. 38, No. 2-3 pp. 203-208.
Cunderliková B, et al., "Modification of extracorporeal photopheresis technology with porphyrin precursors. Comparison between 8-methoxypsoralen and hexaminolevulinate in killing human T-cell lymphoma cell lines in vitro." Biochimica et Biophysica Acta (BBA) General Subjects, Jun. 8, 2014, vol. 1840, No. 9, pp. 2702-2708.
David M. Ward, "Extracorporeal photopheresis: How, when, and why", Journal of Clinical Apheresis, Aug. 1, 2011, vol. 26, No. 5, pp. 276-285.
Susan Shahzidi, et al., "Simultaneously targeting mitochondria and endoplasmic reticulum by Photodynamic therapy induces apoptosis in human lymphoma cells", Photochemical and Photobiological Sciences, Jan. 1, 2011, vol. 10, No. 11, p. 1773.
Qian Peng, "Editorial: Photodynamic Therapy and Detection", Journal of Environmental Pathology, Toxicology and Oncology, Jan. 1, 2006 vol. 25, No. 1-2, pp. 1-6.
N F Gamaleia, "Sensitivity of normal and malignant human lymphocytes to 5-aminolevulinic acidmediated photodynamic damage", Exp Oncol, Mar. 1, 2008, vol. 30, No. 1, pp. 65-69.
H. Peter Van Iperen, et al., "Singlet oxygen producing photosensitizers in photophoresis", Journal of Photochemistry and Photobiology, Apr. 1, 1997, vol. 38, No. 2-3, pp. 203-208.

(Continued)

*Primary Examiner* — Mark Halvorson
*Assistant Examiner* — Kauser M Akhoon
(74) *Attorney, Agent, or Firm* — John P. White; Cooper & Dunham LLP

(57) ABSTRACT

The present invention relates to the use of a photoactivatable Porphyrin-Derivative in extracorporeal photophoresis (ECP) treatment, in which a patient's blood or part of it containing sad Porphyrin-derivative is/are exposed to light of a wavelength which activates said photoactivatable Porphyrin-Derivative.

13 Claims, 13 Drawing Sheets

(56) References Cited

OTHER PUBLICATIONS

Figure 1A:
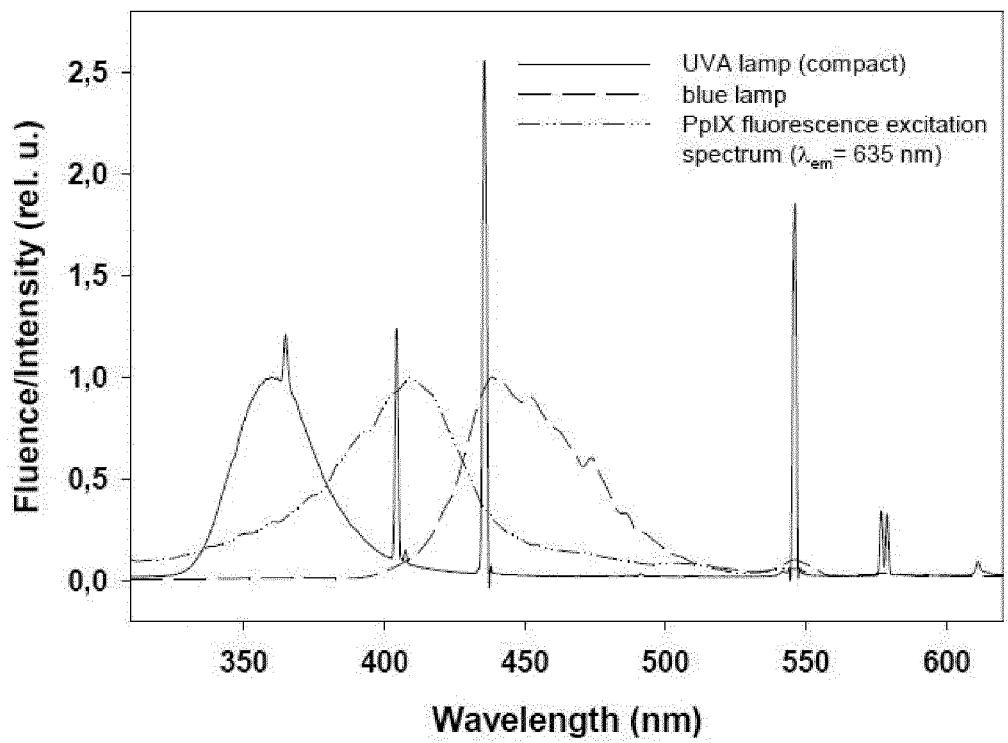

PCT International Search Report(Form PCT/ISA/210), dated Jul. 6, 2015.
PCT Written Opinion of the International Searching Authority, dated Jul. 6, 2015.
Oct. 25, 2018 Communication pursuant to Article 94(3) EPC, in connection with corresponding European Application No. 15 718 489.6.
Notice of Reasons for Refusal dated Jan. 22, 2019 in connection with corresponding Japanese Patent Application JP 2017-507079.
Akita et al., "The effect of psoralen plus ultraviolet A *in vitro* in HUT-78 enhances by 5-aminolevulinic acid", Journal Compilation, 2007, vol. 23, pp. 95-97.
Garban et al., "Extracorporeal photopheresis as a curative treatment strategy in non epidermotropic T-cell lymphoma and large granular lymphocyte leukemia", Annals of Oncology, 2012, vol. 23, pp. 2386-2390.

\* cited by examiner

8-MOP concentration (μM)

Time (min)

control 1.0 µM 8-MOP/10 min UV-A 5.0 µM HAL/10 min UV-A 7.4 µM HAL/10 s blue light 0.1 µM 8-MOP+1.55 µM HAL/10 min UV-A

Fig. 14

|  | 1 hour (CD4+/CD8+) | | | 20 hours (CD4+/CD8+) | | |
|---|---|---|---|---|---|---|
|  | Control | 5-ALA | 8-MOP | Control | 5-ALA | 8-MOP |
| Patient-1 | 89.7/95.8 | 73.7/85.1 | 87.3/94.2 | 72.2/61.6 | 4.3/0.0 | 57.2/56.9 |
| Patient-2 | 79.8/83.6 | 52.1/53.1 | 78.4/84.7 | 40.4/16.3 | 1.2/0.3 | 13.3/5.8 |
| Patient-3 | 78.4/82.2 | 78.0/76.1 | 81.3/78.1 | 45.8/35.0 | 6.2/0.7 | 18.2/15.7 |
| Patient-4 | 48.3/31.3 | 56.4/35.7 | 53.6/30.6 | 27.7/22.5 | 6.4/1.0 | 12.0/8.8 |

MODIFICATION OF EXTRACORPOREAL PHOTOPHERISIS TECHNOLOGY WITH PORPHYRIN PRECURSORS

CROSS-REFERENCE TO RELATED APPLICATIONS

This application is a § 371 national stage of PCT International Application No. PCT/EP2015/058986, filed Apr. 24, 2015, claiming priority of United Kingdom Patent Application No. 1407296.1, filed Apr. 24, 2014, the content of each of which is hereby incorporated by reference into the application.

FIELD OF THE INVENTION

The present invention relates to the use of a photoactivatable Porphyrin-Derivative in extracorporeal photopheresis (ECP) treatment, in which a patient's blood or part of it containing said Porphyrin-derivative is/are exposed to light of a wavelength which activates said photoactivatable Porphyrin-Derivative.

BACKGROUND OF THE INVENTION

Extracorporeal photopheresis (ECP) is a form of apheresis and photodynamic therapy (PDT) where leucocytes (white blood cells) are separated from whole blood and exposed to photoactive 8-methoxypsoralen (8-MOP) as a photosensitiser and ultraviolet-A (UV-A) light before reintroduced back to the patient's circulation. ECP has for more than two decades been approved for the treatment of cutaneous T-cell lymphomas (CTCL) [1]. CTCL represents a heterogenous group of non-Hodkin's lymphoma while GVHD is a complication that can occur after stem cell or bone marrow transplantation in which immune cells attack the transplant recipient's body.

In addition, a number of T-cell-mediated diseases are being explored as suitable indications for ECP, including cGvHD, rejection of transplanted organs and certain autoimmune disorders. Today Therakos Photopheresis System, a device designed for this modality by the Therakos, Inc., is used at more than 150 university medical centers in US and Europe with more than 250,000 treatments so far.

Briefly, the basic procedure of ECP starts with an insertion of an intravenous line into a patient's arm. About 500 mL of blood (10% to 15% of the whole blood) are then withdrawn and collected with an anticoagulant in the Therakosis Photopheresis System. The white blood cells (mainly lymphocytes) are separated by centrifugation over a number of cycles. The leukocyte rich fraction is then treated with a sterile solution of 8-MOP as a photosensitiser and exposed to UVA irradiation, followed by returning the treated leukocytes to the patient. Red blood cells and plasma are returned to the patient between each cycle [2, 3].

In CTCL 8-MOP is thought to bind covalently to DNA in the separated leucocytes resulting in cell cycle arrest and apoptosis. However, risk of the development of cutaneous malignances after the use of psoralens under the conditions of PUVA (psoralen plus UV-A) therapy has been suggested [4]. 8-MOP binds to DNA of not only neoplastic cells, but also normal cells, thus increasing potential risk of carcinogenesis. Moreover, 8-MOP induces cell death to both tumour and normal cells with no selectivity after UV-A light exposure. In addition, the exclusive use of UV-A light to photoactive 8-methoxypsoralen (8-MOP) as a photosensitiser is under certain circumstances also potentially disadvantageous due to health risks carried by use of UV light.

It was thus the basic intention of this invention to improve on this situation and find one or more substitutes for 8-MOP for use in ECP.

This invention is based on the finding that compounds traditionally used in ECP can be replaced by a photoactivatable Porphyrin-Derivative. It was thus found that Hexaminolevulinate(HAL)-induced protoporphyrin-IX, a potent photosensitiser, localises outside of cell nucleus and that in a HAL-mediated photodynamic therapy activated/transformed lymphocytes are selectively destroyed and that this therapy induces systemic anti-tumour immunity. In addition, in a HAL-mediated photodynamic therapy it is possible to use UV-A and "blue" (visible) light leading to induction of both apoptosis and necrosis, whereas traditional 8-MOP therapy uses only UV-A and induces apoptosis only. Finally, a HAL-mediated photodynamic process using UV-A light clearly kills lymphocytes from GvHD and CTLC patients more efficiently than 8-MOP. Accordingly, 8-MOP can be replaced in ECP by photoactivatable Porphyrin-Derivatives and thus also by HAL (that induces synthesis of a protoporphyrin-IX).

SUMMARY OF THE INVENTION

In summary, this invention is based on the finding that compounds traditionally used in ECP can be replaced by a photoactivatable Porphyrin-Derivative. These photoactivatable Porphyrin-Derivative include also Porphyrins or Protoporphyrins whose synthesis is induced by 5-aminolevulinic acid (ALA) or an ester thereof like hexaminolevulinate (HAL) so that these compounds are incorporated into the Porphyrin-Derivative, thus including Hexaminolevulinate-induced protoporphyrin-IX.

The invention is thus directed to the use of a photoactivatable Porphyrin-Derivative in extracorporeal photopheresis (ECP) treatment, in that a patient's blood or part of it containing said photoactivatable Porphyrin-derivative is/are exposed to light of a wavelength which activates said photoactivatable Porphyrin-Derivative.

This wavelength of the light activating the compound is selected from a wave length of between and including 100 nm and 1000 nm which includes the ranges of 315 nm and 630 nm, 315 and 495 nm or 315 nm and 450 nm or those of between and including 315 nm and 380 nm (UV-A) or 380 and 450 nm ("blue light").

Said Porphyrin-Derivative can be selected from known non-naturally occurring Porphyrin-Derivative like Benzoporphyrin derivative monoacid ring A (BPD-MA; Vysudyne®, Verteporfin®), Tetra (metahydroxyphenyl) chlorin (mTHPC; Foscan®), Porfimer sodium (Photofrin®), Chlorin e6, Pd-bacteriopheophorbide (Tookad®), or 2-(1-hexyloxyethyl)-2-devinyl pyropheophorbide-a (HPPH; Photochlor®).

In addition and as said above, said Porphyrin-Derivative can be selected from a Porphyrin-Derivative being derived from an ALA-Compound (5-aminolevulinic acid (ALA) or an ester thereof like hexaminolevulinate) like protoporphyrin IX or a protoporphyrin/porphyrin being induced by an ALA-Compound like hexaminolaevulinate-induced protoporphyrin-IX.

Thus, the invention can—in a sub-aspect—also be considered as being directed to the use an ALA-Compound (5-aminolevulinic acid or an ester thereof or a salt of said acid or ester) in an extracorporeal photophoresis treatment by exposing a patient's blood or part of it having been brought in contact with said 5-aminolevulinic acid, said ester or said salt (said ALA-Compound) to light of a wavelength of between and including 100 nm and 1000 nm. This wavelength of the light activating the compound is selected from a wave length of between and including 100 nm and 1000 nm which includes the ranges of 315 nm and 630 nm, 315 and 495 nm or 315 nm and 450 nm or those of between and including 315 nm and 380 nm (UV-A) or 380 and 450 nm ("blue light"). The ALA-Compound is most often 5-aminolevulinic acid (ALA) or a salt thereof as well as ALA-methyester (methyl-aminolevulinate) or especially ALA-hexylester (hexaminolevulinate; hexyl 5-amino-4-oxopentanoate; HAL) or a salt thereof.

Said extracorporeal photophoresis (ECP) treatment is mostly aimed at treating cancer, lymphocyte-mediated malignant and non-malignant disorders, T-Cell-mediated diseases, autoimmune diseases and/or infections or at stimulating and/or modulating an immunological response against malignacies and immunological diseases. This especially includes lymphoma like cutaneous T-cell lymphoma or erythrodermic cutaneous T-cell lymphoma.

Just as in the traditional ECP treatment known in the art, also in most cases of the ECP treatment of this invention, blood is withdrawn and collected from a patient. The white blood cells (mainly lymphocytes) are separated by centrifugation over a number of cycles. The leukocyte rich fraction (in this case said part of patient's blood) containing said Porphyrin-Derivative exposed to light irradiation, followed by returning the treated leukocytes (the treated part of patient's blood) to the patient. Red blood cells and plasma (the remaining part of patient's blood) are returned to the patient between each cycle. In a very common use according to the invention said part of patient's blood (e.g. the leukocyte rich fraction) is then treated with said Porphyrin-Derivative or with said ALA-Compound (then followed by an incubation period of 30 to 120 min so that the induced synthesis of Porphyrin-Derivative is completed). It is also possible that said Porphyrin-Derivative or ALA-Compound had previously been applied systemically (orally or intravenously) to the patient. After systemic administration—in an alternative use of the invention as claimed herein which uses the ECP approach—the body of the patient may also be exposed to light like e.g. exposure of the skin after administration of ALA.

DETAILED DESCRIPTION

The invention is thus in its broadest aspect directed to a photoactivatable Porphyrin-Derivative for use in an extracorporeal photophoresis treatment by exposing a patient's blood or part of it containing said photoactivatable Porphyrin-Derivative to light of a wavelength which activates said photoactivatable Porphyrin-Derivative.

In another embodiment of this broad aspect of the invention the invention is also directed to the use of a photoactivatable Porphyrin-Derivative in the manufacture of a medicament for treatment of a patient by extracorporeal photophoresis by exposing said patient's blood or part of it containing said photoactivatable Porphyrin-Derivative to light of a wavelength which activates said photoactivatable Porphyrin-Derivative.

The invention thus also covers in its broadest aspect a method of treatment of a patient in need thereof, wherein said method comprises:
 a) administering a photoactivatable Porphyrin-Derivative to the blood of a patient (or a part thereof) wherein said patient is in need of treatment,
 b) treating said patient's blood (or a part thereof) of step a) with light of a wavelength which activates said photoactivatable Porphyrin-Derivative and
 c) administering at least a portion of said patient's blood (or part thereof) from step b) to said patient.

In an often preferred embodiment according to this broadest aspect of the invention said wavelength which activates said photoactivatable Porphyrin-Derivative is between and including 100 nm and 1000 nm.

The invention is also directed to an ALA-Compound being a 5-aminolevulinic acid or an ester thereof or a salt of said acid or ester for use in an extracorporeal photophoresis treatment by exposing a patient's blood or part of it having been brought in contact with said 5-aminolevulinic acid, said ester or said salt (said ALA-Compound) to light of a wavelength of between and including 100 nm and 1000 nm.

In one embodiment the proviso applies that the extracorporeal photophoresis treatment is not for the inactivation of pathogens, especially not of pathogens selected from viruses or bacteria like HIV-1, HIV-2, hepatitis B or C or bacteria produced by "produits sanguine labile" (PSL).

In one embodiment the proviso applies that the extracorporeal photophoresis treatment is not for the treatment of blood platetelet concentrates for blood transfusions, especially blood transfusions following chemotherapy or surgical intervention or thrombocytopenia.

In another embodiment of this use of an ALA-Compound the invention is thus also directed to the use of an ALA-Compound in the manufacture of a medicament for treatment of a patient by extracorporeal photophoresis by exposing said patient's blood or part of it having been brought in contact with said ALA-Compound to light of a wavelength of between and including 100 nm and 1000 nm.

The invention thus also covers regarding such use of an ALA-Compound a method of treatment of a patient in need thereof, wherein said method comprises:
 a) administering an ALA-Compound to the blood of a patient (or a part thereof) wherein said patient in need of treatment,
 b) treating said patient's blood (or a part thereof) of step a) with light of a wavelength of between and including 100 nm and 1000 nm and
 c) administering at least a portion of said patient's blood (or part thereof) from step b) to said patient.

The invention is also directed to an ALA-Compound being a 5-aminolevulinic acid or an ester thereof or a salt of said acid or ester for use in an extracorporeal photophoresis treatment by exposing a patient's blood or part of it having been brought in contact with said 5-aminolevulinic acid, said ester or said salt to light of a wavelength of between and including 315 nm and 450 nm,
wherein said extracorporeal photophoresis treatment is for the treatment of cancer, lymphocyte-mediated malignant and non-malignant disorders, T-Cell-mediated diseases, autoimmune diseases or for modulating an immunological response against malignacies and immunological diseases.

In an often preferred embodiment of this use of an ALA-Compound according to the invention, said ALA-Compound used according to the invention is a compound of formula I,

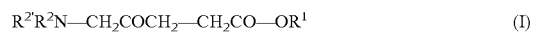

wherein $R^1$ may represent alkyl optionally substituted by hydroxy, alkoxy, acyloxy, alkoxycarbonyloxy, sulpho, amino, aryl, oxo or halogen groups and optionally interrupted by oxygen, nitrogen, sulphur or phosphorus atoms; and wherein $R^2$ and $R^{2'}$ independently of each other represent a hydrogen atom or alkyl optionally substituted by hydroxy, alkoxy, acyloxy, alkoxycarbonyloxy, amino, aryl, oxo or halogen groups and optionally interrupted by oxygen, nitrogen, sulphur or phosphorus atoms.

In a preferred embodiment the alkyl being optionally substituted as defined above is selected from $C_{1-12}$-alkyl, $C_{1-10}$-alkyl, $C_{1-8}$-alkyl or $C_{1-6}$-alkyl and thus may be optionally substituted methyl, ethyl, propyl, butyl, pentyl, hexyl, heptyl, octyl, nonyl, decyl, undecyl, or dodecyl.

In another potentially related preferred embodiment the substituents may be selected from —OH, —SH, —$NH_2$, =O, —$OCH_3$, —$OC_2H_4$, —$OC_3H_7$, —$OC_4H_9$, —C(O)$OCH_3$, —C(O)$C_2H_5$, F, Cl, Br, I, benzyl, or phenyl, most preferably may be selected from —OH, —SH, —$NH_2$, =O, —F, —Cl, —$OCH_3$, —$OC_2H_4$, —$OC_3H_7$, —$OC_4H_9$, or —C(O)$OCH_3$.

In an often preferred embodiment of this use of an ALA-Compound according to the invention, said ALA-Compound used according to the invention is selected from 5-aminolevulinic acid (ALA) or ALA-methylester, ALA-ethylester, ALA-propylester, ALA-hexylester (hexyl 5-amino-4-oxopentanoate; HAL), ALA-heptylester, ALA-octylester or salts thereof, preferably is 5-aminolevulinic acid (ALA), ALA-methyester (methyl-aminolevulinate) or ALA-hexylester (hexaminolevulinate; hexyl 5-amino-4-oxopentanoate; HAL), more preferably is 5-aminolevulinic acid (ALA) or ALA-hexylester (hexaminolevulinate; hexyl 5-amino-4-oxopentanoate; HAL).

In an often preferred embodiment of this use of said ALA-Compound according to the invention the time between contacting said patient's blood or part of it with said 5-aminolevulinic acid, ester or salt and the exposure to light of said wavelength is between and including 5 min and 480 min, preferably is between and including 15 min and 240 min, more preferably is between and including 30 min and 120 min, most preferably is between and including 45 min and 75 min.

The invention is also directed to a photoactivatable Porphyrin-Derivative for use in an extracorporeal photophoresis treatment by exposing a patient's blood or part of it containing said photoactivatable Porphyrin-derivative to light of a wavelength which activates said photoactivatable Porphyrin-Derivative, wherein said wavelength which activates said photoactivatable Porphyrin-Derivative is between and including 315 nm and 450 nm, wherein said Porphyrin-Derivative is selected from a Porphyrin-Derivative being derived from an ALA-Compound (as described above), preferably being protoporphyrin IX, ALA-induced protoporphyrin IX, or hexaminolaevulinate-induced protoporphyrin IX; and wherein said extracorporeal photophoresis treatment is for the treatment of cancer, lymphocyte-mediated malignant and non-malignant disorders, T-Cell-mediated diseases, autoimmune diseases or for modulating an immunological response against malignacies and immunological diseases.

In an often preferred embodiment according to the most broad aspect of the invention the photoactivatable Porphyrin-Derivative used according to the invention said Porphyrin-Derivative is selected from a Porphyrin-Derivative being derived from an ALA-Compound as described and used above according to the invention, preferably being protoporphyrin IX, a protoporphyrin/porphyrin being induced by an ALA-Compound as described above, or hexaminolaevulinate-induced protoporphyrin-IX.

The biological basis of these ALA-Compounds being porphyrin precursors e.g. 5-aminolevulinic acid (ALA) or its hexylester (HAL) can be found in [5-8]. In the cells, ALA is formed from glycine and succinyl CoA at the beginning of the heme biosynthetic pathway. In the last step of this pathway, iron is incorporated into an intermediate product protoporphyrin IX (PpIX) to form heme. The PpIX is a potent photosensitiser and may accumulate in the cells after administration of exogenous ALA [5, 6]. Topically applied ALA is commonly used in PDT of superficial cutaneous malignancies yielding favourable treatment results [5, 6]. Since ALA has a hydrophilic character, more lipophilic ALA esters, including HAL, have been developed to penetrate more easily through cellular membranes [9, 10].

In an often preferred embodiment of the broadest aspect of the invention, said photoactivatable Porphyrin-Derivative used according to the invention is a photosensitizer.

In this often preferred embodiment of the broadest aspect of the invention said photoactivatable Porphyrin-Derivative used according to the invention is selected from a non-naturally occurring Porphyrin-Derivative and preferably is selected from Benzoporphyrin derivative monoacid ring A (BPD-MA; Vysudyne®, Verteporfin®),
Tetra (metahydroxyphenyl) chlorin (mTHPC; Foscan®),
Porfimer sodium (Photofrin®),
Tin ethyletiopurpurin (SnET2; Purlytin®),
Pc4,
Hematoporphyrin derivative (HPD),
2-(1-hexyloxyethyl)-2-devinyl pyropheophorbide-a (HPPH; Photochlor),
Mono-N-aspartyl chlorin e6 (NPe6, Talporfin®),
Chlorin e6 conjugated with polyvinyl pyrrolidone (Foto-lon®),
Pd-bacteriopheophorbide (Tookad®),
Lutetium-texaphyrin (Lu-tex; Lutrin®),
Boronated porphyrin (BOPP),
Hypericin (VIMRxyn),
Sulphonated aluminium phthalocyanine (AlPcS; Photo-sense®),
Porphycene (ATMPn) or
Dibromorhodamine derivative (TH9402).

In another preferred embodiment of the broadest aspect of the invention, said photoactivatable Porphyrin-Derivative used according to the invention being selected from a non-naturally occurring Porphyrin-Derivative is preferably is selected from Benzoporphyrin derivative monoacid ring A (BPD-MA; Vysudyne®, Verteporfin®),
Tetra (metahydroxyphenyl) chlorin (mTHPC; Foscan®),
Porfimer sodium (Photofrin®),
Chlorin e6,
Pd-bacteriopheophorbide (Tookad®), or
2-(1-hexyloxyethyl)-2-devinyl pyropheophorbide-a (HPPH; Photochlor®).

"Photoactivatable" is defined—according to the invention—as an ability of a compound to be activated by light of a wavelength of between and including 100 nm to 1000 nm. This is to be understood that photoactivatable compounds are highly conjugated systems with intensive absorption bands at said wavelength.

"Photoactivatable Porphyrin-Derivative" is defined—according to the invention—as photoactivatable compound being structurally related to a porphyrin. Thus, it has the ability to be activated by light of a wavelength of between and including 100 nm to 1000 nm and is a highly conjugated system with intensive absorption bands at said wavelength. In most cases it is a Photosensitizer as defined below. By definition it is most often a compound comprising a porphyrin ring system in its structure or may be a protoporphyrin. It may for example be protoporphyrin IX. Besides being a photosensitizer as defined below it may also be a protoporphyrin/porphyrin being induced by an ALA-Compound as described above. One possible example is an ALA-induced protoporphyrin IX in which—at least some of—the ALA (5-aminolevulinic acid or a salt thereof) is incorporated into (becomes part of) the structure of the protoporphyrin during synthesis. Another possible example is a hexaminolaevulinate-induced protoporphyrin-IX in which—at least some of—the hexaminolaevulinate is incorporated into (becomes part of) the protoporphyrin during synthesis.

"Photosensitizer" is defined according to the inventions as a compound that is sensitive to light of a wavelength of between and including 100 nm to 1000 nm and may be activated by this. In most cases this photosensitizer comprises a porphyrin ring in its structure or is a protoporphyrin. Preferably the photosensitizer is selected from Benzoporphyrin derivative monoacid ring A (BPD-MA; Vysudyne®, Verteporfin®), Tetra (metahydroxyphenyl) chlorin (mTHPC; Foscan®), Porfimer sodium (Photofrin®), Tin ethyletiopurpurin (SnET2; Purlytin®), Pc4, Hematoporphyrin derivative (HPD), 2-(1-hexyloxyethyl)-2-devinyl pyropheophorbide-a (HPPH; Photochlor®), Mono-N-aspartyl chlorin e6 (NPe6, Talporfin®), Chlorin e6 conjugated with polyvinyl pyrrolidone (Foto-lon®), Pd-bacteriopheophorbide (Tookad®), Lutetium-texaphyrin (Lu-tex; Lutrin®), Boronated porphyrin (BOPP), Hypericin (VIM-Rxyn), Sulphonated aluminium phthalocyanine (AlPcS; Photosense®), Porphycene (ATMPn) or Dibromorhodamine derivative (TH9402). Most preferably the photosensitizer is selected from Benzoporphyrin derivative monoacid ring A (BPD-MA; Vysudyne®, Verteporfin®), Tetra (metahydroxyphenyl) chlorin (mTHPC; Foscan®), Porfimer sodium (Photofrin®), Chlorin e6, Pd-bacteriopheophorbide (Tookad®), or 2-(1-hexyloxyethyl)-2-devinyl pyropheophorbide-a (HPPH; Photochlor®).

Examples of such photosensitizers with their structures can be found below:

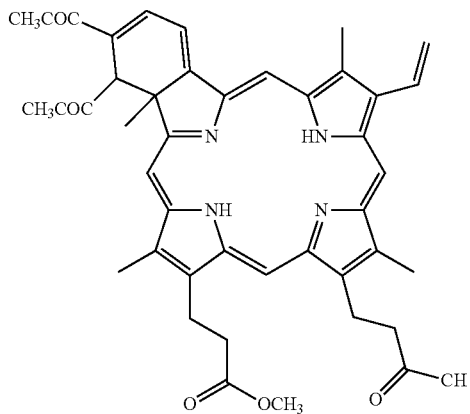

Benzoporphyrin derivative monoacid A
ε (688 nm) = 3.4 × 10$^4$ M$^{-1}$cm$^{-1}$

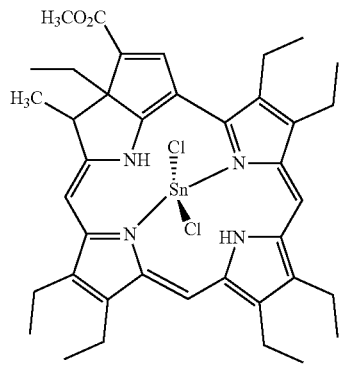

Tin-etio purpurin
ε (637 nm) = 3.9 × 10$^4$ M$^{-1}$cm$^{-1}$

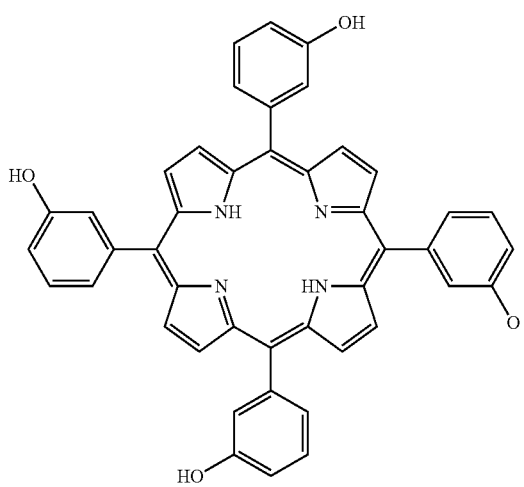

meta-tetrahydroxyphenylchlorin
ε (652 nm) = 2.2 × 10$^4$ M$^{-1}$cm$^{-1}$

-continued
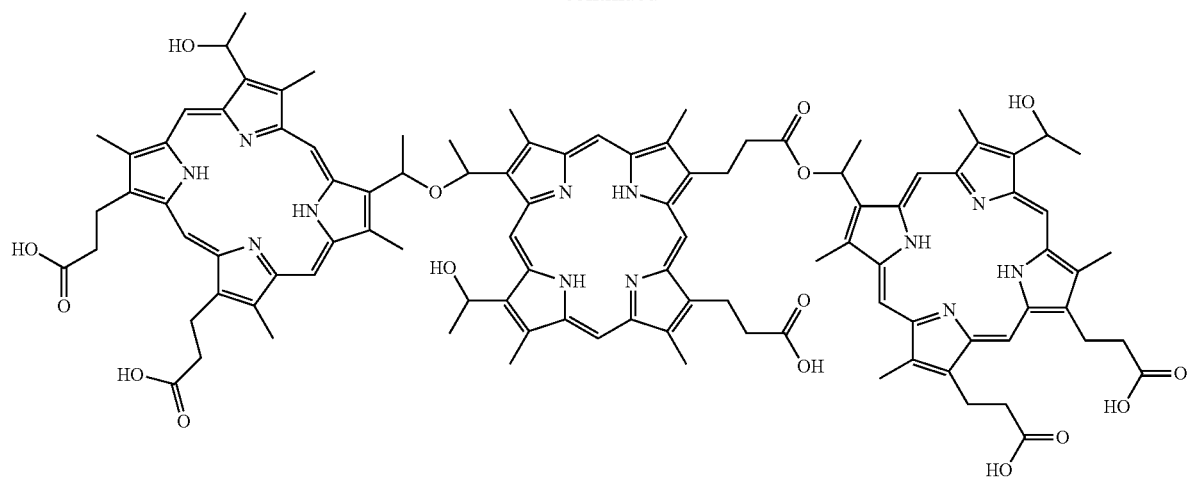
HPD (?), Photofrin (?)
$\varepsilon$ (630 nm) = -2 × 10$^3$ M$^{-1}$cm$^{-1}$ ?
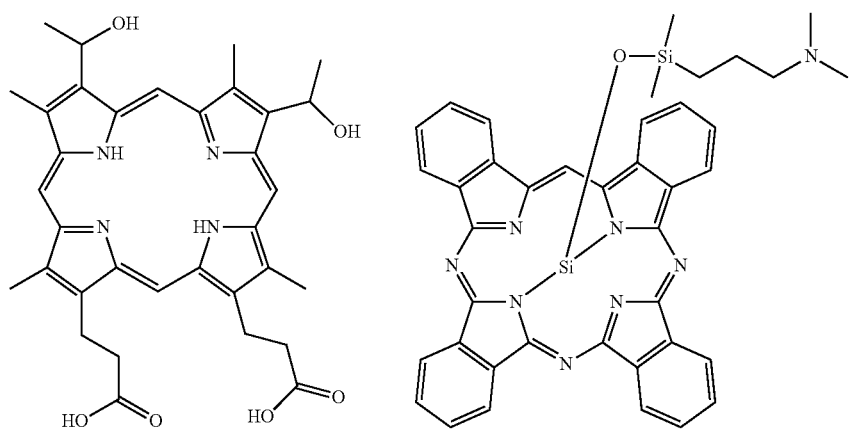
Protoporphyrin IX
$\varepsilon$ (630 nm) = 3 × 10$^5$ M$^{-1}$cm$^{-1}$
Pc4
$\varepsilon$ (670 nm) = 2 × 10$^5$ M$^{-1}$cm$^{-1}$
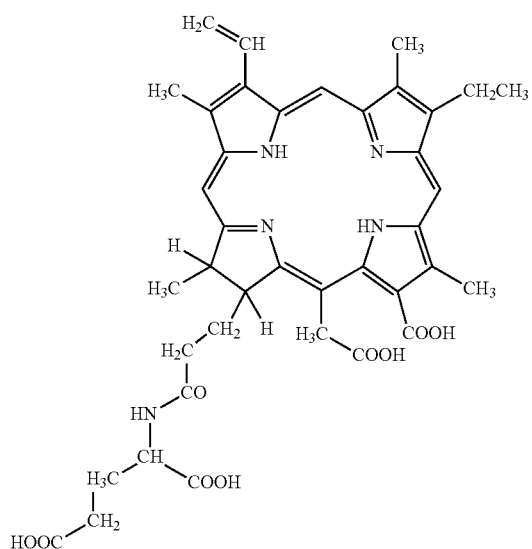
Mono-aspartyl Chlorin c$_6$
$\varepsilon$ (656 nm) = 4 × 10$^4$ M$^{-1}$cm$^{-1}$ A compound like Porphyrin-Derivative "being induced" or that "is induced" is defined—according to the invention—as a compound like a protoporphyrin or porphyrin into whose structure the—or at least some of the—inducing compounds (e.g. the ALA-Compound) is incorporated during synthesis. It most often also induces/increases synthesis of the "induced compound" especially by local increase/accumulation shifting the balance in a rate limiting step. One preferred example is a protoporphyrin like protoporphyrin IX being induced by ALA (5-aminolevulinic acid) or a salt thereof in which some of the ALA is also incorporated into the structure of the protoporphyrin and the local excess of ALA leads to accumulation of the protoporphyrin. Another preferred example is protoporphyrin IX being induced by HAL (hexaminolevulinate) in which some of the HAL is also incorporated into the structure of the protoporphyrin and the local excess of HAL leads to accumulation of the protoporphyrin.

"ALA-Compound" is defined—according to the invention—as 5-aminolevulinic acid or an ester thereof or a salt of said acid or ester and it includes compounds of structure $R^{2'}R^2N$—$CH_2COCH_2$—$CH_2CO$—$OR^1$. Preferred examples are 5-aminolevulinic acid (ALA), ALA-methyester (methyl-aminolevulinate) or ALA-hexylester (hexaminolevulinate; hexyl 5-amino-4-oxopentanoate; HAL). ALA is formed from succinyl CoA and glycine in the first step of heme synthesis. Its increase (and thus that of all ALA-Compounds) leads to a localised build-up of Protoporphyrin IX since the action of ferrochelatase (the metallating enzyme) is the rate limiting step in heme synthesis. Thus, an excess of ALA (and all ALA-Compounds) leads to accumulation of Protoporphyrin IX, a very potent photosensitizing agent/"Photosensitizer". This is to be understood as the protopophyrin IX "being induced" by e.g. ALA (the ALA-induced Protoporphyrin or the ALA-induced Protoporphyrin IX). In principle, ALA-Compounds are Porphyrin precursors. The esters of 5-aminolevulinic acid defined herein as part of the ALA-compound are described in detail in WO96/028412 A1 to which reference is herewith made.

"Extracorporeal photophoresis" (abbreviated "ECP") is defined—according to the invention—as a form of apheresis and photodynamic therapy (PDT). A patient's blood—or in most cases leucocytes (white blood cells) being separated (e.g. by centrifugation) from whole blood—are exposed to a photoactive compound or a compound inducing (forming part and inducing synthesis of; see above) a photoactive compound. Then the blood or part of it e.g. the leucocyte enriched fraction is exposed to light of a wavelength that activates the photoactive compound. Then, the treated blood (or part thereof) is administered back to the patient.

"Extracorporeal photophoresis treatment" is defined—according to the invention—as a treatment of a disease by "extracorporeal photophoresis". Examples include the treatment of cancer, of lymphocyte-mediated malignant and non-malignant disorders, of T-Cell-mediated diseases, of autoimmune diseases or of infections. The "extracorporeal photophoresis treatment" may be also aimed at stimulating or modulating an immunological response against malignacies and immunological diseases. Most pronounced examples include lymphoma, like cutaneous T-cell lymphoma or erythrodermic cutaneous T-cell lymphoma or skin cancer.

"Exposing" is defined—according to the invention—as exposing a substance, e.g. a patient's blood or part thereof, to a certain physical effect, e.g. irradiation by light of a certain wavelength.

"Part of patient's blood" is defined—according to the invention—as either mononuclear/corpuscular elements of a patient's blood or patient's blood in which these mononuclear/corpuscular elements are enriched. Thus, this covers isolated white blood cells, or leukocyte enriched blood, or leukocyte enriched buffy coat. These may have a hematocrit value of 0% to 10% or 2.5% to 7% or may be 5% to 25% or 10% to 30% of the total peripheryl blood mononuclear cell component. The part of patient's blood may be produced by enriching said mononuclear/corpuscular elements in the blood by e.g. centrifugation or filtering. The part that remains after the enrichment of said mononuclear/corpuscular elements in patient's blood is called "remaining part of patient's blood" and is e.g. comprising or consisting of red blood cells (erythrocytes) and plasma.

"Light of a wavelength which activates said photoactivatable Porphyrin-Derivative" is defined—according to the invention—as light of a wavelength of between (and including) 100 nm to 1000 nm. As the photoactivatable Porphyrin-Derivative is a highly conjugated system with intensive absorption bands, this absorption bands define said wavelength which activates said photoactivatable Porphyrin-Derivative.

"Brought in contact with said ALA-Compound" is defined—according to the invention—as treating the patient's blood or part thereof with said ALA-Compound by applying this ALA-Compound to the blood or a part thereof. This is most often done when the blood is outside the patient's body (e.g. by mixing or dissolving) but does in principle also apply if the ALA-compound is systemically (e.g. intravenously or orally) given to the patient so that the blood is put in contact with the ALA-compound inside the body.

In the following, often preferred embodiments of both, the broadest aspect of the invention with said photoactivatable Porphyrin-Derivative or the related aspect of an ALA-Compound, both used according to the invention are described. The fact that these—often preferred—embodiments are applicable to both these related aspects of the invention is indicated by: "In one embodiment of the photoactivatable Porphyrin-Derivative or ALA-Compound used according to the invention". It should also be understood that these embodiments also apply to the respective method of treatment-aspect as well as to the use in the manufacture of a medicament.

In one embodiment of the photoactivatable Porphyrin-Derivative or ALA-Compound used according to the invention said Porphyrin-Derivative or said ALA-Compound is used in combination with a psoralen like 8-methoxypsoralen (8-MOP).

In one embodiment of the photoactivatable Porphyrin-Derivative or ALA-Compound used according to the invention, the wavelength of the light activating the compound is selected from a wave length of between and including 100 nm and 900 nm, 100 nm and 630 nm, 100 nm and 495 nm, 315 nm and 630 nm, 315 and 495 nm, 315 nm and 450 nm, preferably being selected from between and including 315 nm and 495 nm, 315 and 450 nm, 315 nm and 380 nm, 380 and 495 nm, or 380 and 450 nm, more preferably between and including 315 nm and 450 nm or between and including 380 nm and 450 nm.

In one embodiment of the photoactivatable Porphyrin-Derivative or ALA-Compound used according to the invention, the wavelength of the light activating the compound is selected from a wave length of between and including 380 nm and 450 nm.

Light of a wavelength of between (and including)
315 nm and 380 nm is UV-A light
380 and 495 nm is visible light covering violet and blue,
315 nm and 450 nm is UV-A and visible "blue light", and
380 nm and 450 nm is the visible "blue light".

Other embodiments of the photoactivatable Porphyrin-Derivative or ALA-Compound used according to the invention, relate to the time that a patient's blood or part of it containing said photoactivatable Porphyrin-Derivative or having been brought in contact with an ALA-Compound is exposed to light of said certain wavelength. This may differ in a quite broad range from only a few seconds to more than 1 or 2 hours or more. In one case (which might for example apply to cases in which the blood or part thereof is exposed to UV-A light) the exposure time will be between 15 minutes and 120 minutes. In another case (which might for example apply to cases in which the blood or part thereof is exposed to "blue light") the exposure time will be between 5 seconds and 30 minutes.

In the following there are different lists of indications for which the extracorporeal treatment—in which said photoactivatable Porphyrin-Derivative or said ALA-Compound are used according to the invention—may be potentially successfully applied. These lists thus also cover indications for the respective method of treatment-aspect as well as for the use of the medicament to be manufactured according to the invention.

In one embodiment of the photoactivatable Porphyrin-Derivative or ALA-Compound used according to the invention said extracorporeal photophoresis treatment is for the treatment of cancer, lymphocyte-mediated malignant and non-malignant disorders, T-Cell-mediated diseases, autoimmune diseases and/or infections or for stimulating and/or modulating an immunological response against malignacies and immunological diseases; preferably for the treatment of cancer, lymphocyte-mediated malignant and non-malignant disorders, T-Cell-mediated diseases, autoimmune diseases or for modulating (e.g. stimulating or inhibiting) an immunological response against malignacies and immunological diseases.

In one embodiment of the photoactivatable Porphyrin-Derivative or ALA-Compound used according to the invention said extracorporeal photophoresis treatment is for the treatment of cancer.

In one embodiment of the photoactivatable Porphyrin-Derivative or ALA-Compound used according to the invention said extracorporeal photophoresis treatment is for the treatment of
- lymphoma, preferably T-cell lymphoma, most preferably cutaneous T-cell lymphoma or erythrodermic cutaneous T-cell lymphoma; and/or
- haematological cancer, or lymphocyte leukaemia; and/or
- graft versus host disease,
  - like cGVHD following bone marrow transplantation, chronic graft versus host disease (cGvHD) with cutaneous/mucous membrane involvement, chronic graft versus host disease (cGvHD) with hepatic involvement, acute or chronic graft versus host disease with gastrointestinal/pulmonary involvement; and/or
- transplant rejection
  - like solid organ transplant, like lung, renal, or liver transplant, cardiac/heart transplant, heart transplant rejection prophylaxis,
- organ allograft rejection, like cardiac, pulmonary or renal allograft rejection, Bronchiolitis Obliterans Syndrome (BOS) and/or
- multiple sclerosis, systemic sclerosis, progressive systemic sclerosis (PSS), systemic lupus erythematosus (SLE), rheumatoid arthritis, juvenile onset diabetes mellitus, type I diabetes mellitus; and/or
- inflammatory bowel disease, like Crohn's disease or ulcerative colitis; and/or
- inflammatory disorder of the urinary bladder, like cystitits or interstitial cystitis; and/or
- infection other than a retroviral infection, acute or chronic viral infection, HCV or CMV infection, chronic hepatitis C infection; and/or
- AIDS-related complex, HIV-infection disease, Aids related Kaposis, Cervical HPV infection; and/or
- nephrogenic systemic fibrosis and ulcerative colitis, epidermolysis bullosa acquisita; and/or
- pemphigus vulgaris psoriasis, psoriatic arthritis, atopic dermatitis, atopic eczema, lichen planus.

In a preferred embodiment of the photoactivatable Porphyrin-Derivative or ALA-Compound used according to the invention said extracorporeal photophoresis treatment is for the treatment of
- lymphoma, preferably T-cell lymphoma, most preferably cutaneous T-cell lymphoma or erythrodermic cutaneous T-cell lymphoma; and/or
- haematological cancer or lymphocyte leukaemia; and/or
- graft versus host disease,
  - like cGVHD following bone marrow transplantation, chronic graft versus host disease (cGvHD) with cutaneous/mucous membrane involvement, chronic graft versus host disease (cGvHD) with hepatic involvement, acute graft versus host disease with gastrointestinal/pulmonary involvement; and/or
- transplant rejection
  - like solid organ transplant, like lung, renal, or liver transplant, cardiac/heart transplant, heart transplant rejection prophylaxis,
- organ allograft rejection, like cardiac, pulmonary or renal allograft rejection, Bronchiolitis Obliterans Syndrome (BOS) and/or
- systemic lupus erythematosus (SLE), rheumatoid arthritis, juvenile onset diabetes mellitus, type I diabetes mellitus; and/or
- inflammatory bowel disease, like Crohn's disease or ulcerative colitis; and/or
- inflammatory disorder of the urinary bladder, like cystitits or interstitial cystitis; and/or
- infection other than a retroviral infection, acute or chronic viral infection, HCV or CMV infection; and/or
- AIDS-related complex, HIV-infection disease, Aids related Kaposis, Cervical HPV infection; and/or
- pemphigus vulgaris, psoriasis, psoriatic arthritis, atopic dermatitis, atopic eczema, lichen planus;

or more preferably is for the treatment of
- lymphoma, preferably T-cell lymphoma, most preferably cutaneous T-cell lymphoma or erythrodermic cutaneous T-cell lymphoma; and/or
- haematological cancer or lymphocyte leukaemia like B cell or chronic lymphocyte leukaemia; and/or
- graft versus host disease,
  - like cGVHD following bone marrow transplantation, chronic graft versus host disease (cGvHD) with cutaneous/mucous membrane involvement, chronic graft versus host disease (cGvHD) with hepatic involvement, acute graft versus host disease with gastrointestinal/pulmonary involvement; and/or
- transplant rejection like solid organ transplant, like lung, renal, or liver transplant, cardiac/heart transplant, heart transplant rejection prophylaxis, organ allograft rejection, like cardiac, pulmonary or renal allograft rejection, Bronchiolitis Obliterans Syndrome (BOS) and/or systemic lupus erythematosus (SLE), rheumatoid arthritis, juvenile onset diabetes mellitus, type I diabetes mellitus; and/or AIDS-related complex, HIV-infection disease, Aids related Kaposis, Cervical HPV infection; and/or pemphigus vulgaris psoriasis, psoriatic arthritis, atopic dermatitis, atopic eczema, lichen planus.

In one embodiment of the photoactivatable Porphyrin-Derivative or ALA-Compound used according to the invention said extracorporeal photophoresis treatment is for the treatment of lymphoma, preferably T-cell lymphoma, most preferably cutaneous T-cell lymphoma or erythrodermic cutaneous T-cell lymphoma; and/or haematological cancer, or lymphocyte leukaemia.

In one embodiment of the photoactivatable Porphyrin-Derivative or ALA-Compound used according to the invention said extracorporeal photophoresis treatment is for the treatment of graft versus host disease,
like cGVHD following bone marrow transplantation, chronic graft versus host disease (cGvHD) with cutaneous/mucous membrane involvement, chronic graft versus host disease (cGvHD) with hepatic involvement, acute or chronic graft versus host disease with gastrointestinal/pulmonary involvement; and/or transplant rejection
like solid organ transplant, like lung, renal, or liver transplant, cardiac/heart transplant, heart transplant rejection prophylaxis, organ allograft rejection, like cardiac, pulmonary or renal allograft rejection, Bronchiolitis Obliterans Syndrome (BOS).

In one embodiment of the photoactivatable Porphyrin-Derivative or ALA-Compound used according to the invention said extracorporeal photophoresis treatment is for the treatment of multiple sclerosis, systemic sclerosis, progressive systemic sclerosis (PSS), systemic lupus erythematosus (SLE), rheumatoid arthritis, juvenile onset diabetes mellitus, type I diabetes mellitus.

In one embodiment of the photoactivatable Porphyrin-Derivative or ALA-Compound used according to the invention said part of the patient's blood exposed is selected from isolated white blood cells, or leukocyte enriched blood, or leukocyte enriched buffy coat preferably having a hematocrit value of 0% to 10% (or optionally also having a hematocrit value of 2.5% to 7%) and/or having 5% to 25% of the total peripheryl blood mononuclear cell component. In principle, this especially applies if blood (5% to 25%, 5% to 20% or 10% to 15% of the whole blood) are withdrawn from the patient (and optionally combined with an anticoagulant). The white blood cells (mainly lymphocytes) are separated by centrifugation over a number of cycles. This leukocyte rich fraction is the most preferred embodiment of what is covered by "said part of the patient's blood".

In one embodiment of the photoactivatable Porphyrin-Derivative or ALA-Compound used according to the invention said treatment is performed at an interval of once or on two consecutive days per week to once or on two consecutive days per four weeks, or on two consecutive days every two weeks;
and/or
in one embodiment of the photoactivatable Porphyrin-Derivative or ALA-Compound used according to the invention said treatment is performed over a period of between 1 and 12 months, between 2 and 6 months, or for 3 months.

In one embodiment of the photoactivatable Porphyrin-Derivative or ALA-Compound used according to the invention the extracorporal photophoresis treatment is comprising or consisting of the steps of a) Selecting a patient to whom said photoactivatable Porphyrin-Derivative or ALA-Compound has been administered, optionally systemically, like orally or intravenously; and/or b) collecting said patient's blood extracorporeally, optionally mixing it with an anticoagulant; and/or c) enriching one of the mononuclear cell components in said patient's blood like enriching white blood cells to create said part of patient's blood being enriched with said one of the mononuclear cell components and a remaining part, optionally by centrifugation; and/or d) optionally reinfusing—preferably at any time thereafter—said remaining part of patient's blood; and/or e) contacting said patient's blood or said part thereof with said photoactivatable Porphyrin-Derivative or ALA-Compound; and/or f) incubating said patient's blood or said part thereof with said photoactivatable Porphyrin-Derivative or ALA-Compound; and/or g) exposing said patient's blood or said part thereof to light of a wavelength which activates said photoactivatable Porphyrin-Derivative or of a wavelength of between and including 100 nm and 1000 nm, and/or h) reinfusing said treated patient's blood or said treated part thereof preferably wherein the extracorporal photophoresis treatment is comprising or consisting of the steps b) to h), a) to d) and g) to h) or steps b) to e) and g) to h), more preferably wherein in addition, the steps b) to h), steps a) to d) and g) to h) or steps b) to e) and g) to h) are performed in consecutive order in said extracorporal photophoresis treatment.

In one embodiment of the photoactivatable Porphyrin-Derivative or ALA-Compound used according to the invention the extracorporal photophoresis treatment is comprising or consisting of the steps of b) Collecting said patient's blood extracorporeally, optionally mixing it with an anticoagulant; and c) enriching one of the mononuclear cell components in said patient's blood like enriching white blood cells to create said part of patient's blood being enriched with said one of the mononuclear cell components and a remaining part, optionally by centrifugation; and d) reinfusing—preferably at any time hereafter—said remaining part of patient's blood; and e) contacting said patient's blood or said part thereof with said photoactivatable Porphyrin-Derivative or ALA-Compound; and f) incubating said patient's blood or said part thereof with said photoactivatable Porphyrin-Derivative or ALA-Compound; and g) exposing said patient's blood or said part thereof to light of a wavelength which activates said photoactivatable Porphyrin-Derivative or of a wavelength of between and including 100 nm and 1000 nm, and h) reinfusing said treated patient's blood or said treated part thereof.

It is preferred if the steps are performed in consecutive order in said extracorpal photophoresis treatment.

In one embodiment of the ALA-Compound used according to the invention the extracorporal photophoresis treatment is comprising or consisting of the steps of b) Collecting said patient's blood extracorporeally, optionally mixing it with an anticoagulant; and
c) enriching one of the mononuclear cell components in said patient's blood like enriching white blood cells to create said part of patient's blood being enriched with said one of the mononuclear cell components and a remaining part, optionally by centrifugation; and
d) reinfusing—preferably at any time thereafter—said remaining part of patient's blood; and
e) contacting said patient's blood or said part thereof with said ALA-Compound; and
f) incubating said patient's blood or said part thereof with said ALA-Compound; and
g) exposing said patient's blood or said part thereof to light of a wavelength of between and including 100 nm and 1000 nm, and
h) reinfusing said treated patient's blood or said treated part thereof.

It is preferred if the steps are performed in consecutive order in said extracorpal photophoresis treatment.

In one embodiment of the photoactivatable Porphyrin-Derivative used according to the invention the extracorporal photophoresis treatment is comprising or consisting of the steps of b) Collecting said patient's blood extracorporeally, optionally mixing it with an anticoagulant; and
c) enriching one of the mononuclear cell components in said patient's blood like enriching white blood cells to create said part of patient's blood being enriched with said one of the mononuclear cell components and a remaining part, optionally by centrifugation; and
d) reinfusing—preferably at any time hereafter—said remaining part of patient's blood; and
e) contacting said patient's blood or said part thereof with said photoactivatable Porphyrin-Derivative; and
g) exposing said patient's blood or said part thereof to light of a wavelength which activates said photoactivatable Porphyrin-Derivative, and
h) reinfusing said treated patient's blood or said treated part thereof.

It is preferred if the steps are performed in consecutive order in said extracorpal photophoresis treatment.

In one embodiment of the photoactivatable Porphyrin-Derivative or ALA-Compound used according to the invention the extracorporal photophoresis treatment is comprising or consisting of the steps of a) selecting a patient to whom said photoactivatable Porphyrin-Derivative or ALA-Compound has been administered, optionally systemically, like orally or intravenously; and
b) collecting said patient's blood extracorporeally, optionally mixing it with an anticoagulant; and
c) enriching one of the mononuclear cell components in said patient's blood like enriching white blood cells to create said part of patient's blood being enriched with said one of the mononuclear cell components and a remaining part, optionally by centrifugation; and
d) reinfusing—preferably at any time hereafter—said remaining part of patient's blood; and g) exposing said patient's blood or said part thereof to light of a wavelength which activates said photoactivatable Porphyrin-Derivative or of a wavelength of between and including 100 nm and 1000 nm, and
h) reinfusing said treated patient's blood or said treated part thereof.

It is preferred if the steps are performed in consecutive order in said extracorpal photophoresis treatment.

In one further embodiment of these, especially suited for the methods of treatment described above using said photoactivatable Porphyrin-Derivative or said ALA-Compound according to the invention the extracorporal photophoresis treatment comprises the step a) Administering to said patient said photoactivatable Porphyrin-Derivative or ALA-Compound, optionally systemically, like orally or intravenously.

In one embodiment of the photoactivatable Porphyrin-Derivative or ALA-Compound used according to the invention the compound used is 5-aminolevulinic acid (ALA) or ALA-hexylester (hexaminolevulinate; hexyl 5-amino-4-oxopentanoate; HAL),
preferably at a concentration between 0.1 and 10 mM or 0.5 and 5 mM or at 1 mM in said patient's blood or part thereof or at a concentration of between 0.1 and 10 mg/kg or 0.5 mg/kg and 5 mg/kg or 0.75 and 2 mg/kg of body weight, and/or
in the absence of serum or in the presence of 5 to 20% or 10% serum; and/or
with the time between contacting said patient's blood or part of it with ALA or HAL or salt thereof and the exposure to light of said wavelength is between and including 30 min to 120 min, 45 min and 75 min or 1 hour; and/or
said wavelength of the light is of between and including 315 nm and 1000 nm or between and including 315 and 850 nm, preferably between and including 315 nm and 380 nm, between and including 380 and 450 nm, or between and including 315 and 450 nm;
said light having a dose between and including 0.01 and 20 J/cm$^2$.

Another aspect of the invention refers to a kit for use in extracorporal photophoresis or an extracorporal photophoresis treatment comprising a container comprising said photoactivatable Porphyrin-Derivative or ALA-Compound and an instruction leaflet. Preferably, the container comprises said ALA-Compound like ALA or HAL. It may also comprise an anticoagulant and/or 8-MOP.

The present invention is illustrated below with the aid of examples. These illustrations are given solely by way of example and do not limit the general spirit of the present invention.

EXAMPLES

Abstract (Relates to Example 1)

Background: Extracorporeal photopheresis that exposes isolated white blood cells to 8-methoxypsoralen (8-MOP) and ultraviolet-A (UV-A) light is used for the management of cutaneous T-cell lymphomas and graft-versus-host disease. 8-MOP binds to DNA of both tumour and normal cells, thus increases the risk of carcinogenesis of normal cells and after UV-A kills both tumour and normal cells with no selectivity. Hexaminolevulinate (HAL)-induced protoporphyrin-IX is a potent photosensitiser that localises at membranous structures outside of the nucleus of a cell. HAL-mediated photodynamic therapy selectively destroys activated/transformed lymphocytes and induces systemic anti-tumour immunity. The aim of the present study was to explore the possibility of using HAL instead of 8-MOP to kill cells after UV-A exposure.

Methods: Human T-cell lymphoma Jurkat cell line was used to evaluate cell photoinactivation after 8-MOP and/or HAL plus UV-A or blue light with cell proliferation and long term survival assays. The mode of cell death was also analysed by fluorescence microscopy.

Results: Cell proliferation was decreased by HAL/UV-A, HAL/blue light, 8-MOP/UV-A or HALJ8-MOP/UV-A. At sufficient doses, the cells were killed by all the regimens; however, the mode of cell death was dependent on the treatment conditions. 8-MOP/UV-A produced apoptotic death exclusively; whereas both apoptosis and necrosis were induced by HAL/UV-A or HAL/blue light.

Conclusion: 8-MOP can be replaced by HAL to inactivate the Jurkat cells after UV-A irradiation via apoptosis and necrosis. This finding may have an impact on improved efficacy of photopheresis.

Abbreviations: ALA—5-aminolevulinic acid, CTCL—cutaneous T-cell lymphoma, ECP—extracorporeal photopheresis, FBS—fetal bovine serum, HAL—hexaminolevulinate, GVHD—graft-versus-host disease, MOP—methoxypsoralen, MTS—4,5.dimethylthiazol-2-yl)-5-(3-carboxymethoxyphenyl)-2-(4-sulfophenyl)-2 Htetrazolium, PDT—photodynamic therapy, PI—propidium iodide, PpIX—protoporphyrin IX, PUVA—psoralen plus ultraviolet-A, UV—ultraviolet Introduction The main advantage of using ALA or HAL for ECP would be that ALA/HAL-induced PpIX as a potent photosensitiser localises at membranous structures outside of the cell nucleus [5] thus decreasing the risk of potential carcinogenesis as compared to 8-MOP. Moreover, ALA/HAL-induced PpIX after light exposure selectively destroys activated/transformed lymphocytes [11-13]. In addition, PDT can induce systemic anti-tumour immunity (e.g. [14, 15]).

Clinically, topically applied ALA-PDT is already an approved treatment modality for actinic keratosis and superficial basal cell carcinoma of the skin [16-18]). Systemic administration of ALA is also widely used for the PpIX fluorescence-guided resection of malignant glioma [19-22]) and the PDT treatment of dysplasia in Barrett's oesophagus [23-25]).

ALA is a naturally occurring amino acid and has shown little dark toxicity in its clinical uses. Generally, topical application of ALA with a dose of 20% for shorter than 3 hours does not cause generalised photosensitisation. In the case of systemic administration the LD50 has been found to be 2,500 mg/kg body weight (b.w) in mice and rats after a single dose of oral or intraperitoneal administration of ALA [26]). No observable toxic effects have been obtained after a single dose of intravenous injection of 500 mg/kg and 250 mg/kg ALA in mice and rats, respectively 26]). In humans, a single oral dose of 20 mg/kg ALA in drinking water is normally administered for the fluorescence-guided resection of glioma [19-22]); while that of 60 mg/kg is also orally given for the PDT treatment of Barrett's oesophagus [23-25]). The most common side effects from oral ALA are nausea, vomiting and a transient rise in liver enzymes that normally resolves after 48 hours [27].

The potential of using ALA for PDT in animal tumour models was investigated since [28, 29]), followed since 1990 by clinical trials in the PDT treatment of tumours of the human skin and gastrointestinal tract after topical or systemic administration of ALA [16-18, 30, 31]. In 1996, it was found that ALA-PDT could induce apoptosis in carcinoma cells [32, 33]). This finding was further confirmed in several human leukemia and lymphoma cell lines using hexylester of ALA (HAL) [7, 8, 34].

In one preceeding experiment to the invention, the inventors used HAL in PDT to purge tumour cells from the bone marrow in clinically relevant animal models with leukemia or metastasized breast carcinoma and obtained promising results [35, 36].

It was a basic finding of this invention that there is a selective production of PpIX from ALA or its esters in the transformed or activated lymphocytes compared to much less PpIX formed in those normal resting counterparts.

Recently, the inventors found that HAL in combination with an UV-A lamp (with almost identical emission spectra to those of the UV-A lamp used in the existing commercial Therakos photopheresis system) can effectively kill the Jurkat human T-cell lymphoma cell line in vitro (this application), suggesting the possibility of using ALA or its esters for ECP.

The advantages of using ALA for ECP can be summarized as follows:
a. Proliferative (transformed or activated) T-cells produce about 15-fold more ALA-induced PpIX than normal resting T-cells. As a result, those proliferative T-cells are more selectively destroyed after light, unlike the non-selective effects of 8-MOP.
b. ALA-induced PpIX localises at only membranous structures outside of the cell nucleus, thus causing no carcinogenesis.
c. Membrane targeting produces more potent antigenic molecules than DNA-binding 8-MOP. HAL-PDT ex vivo of 4T1 mouse breast carcinoma has suggested to induce systemic anti-tumour immunity in mice [37].
d. ALA is an approved drug with a good safety profile. More than 95% of the Jurkat human T-cell lymphoma cells can be killed after incubation with 1 mM ALA for 1 hour in the presence of 10% foetal bovine serum followed by UVA light exposure. In a typical clinical setting, this corresponds to a dose of approximately 1 mg/kg, which is far below the safe doses used in the clinical ALA applications [19-25].
e. The compatibility of ALA with the current procedure using the Therakos Photopheresis System should be similar to that with 8-MOP. The only difference should be that a patient has to wait for one hour for ALA incubation before UVA light exposure.

The inventors have used the human T-cell lymphoma Jurkat cell line as an in vitro model of cutaneous T-cell lymphoma to test the possibility of using HAL in combination with UV-A to inactivate the cells. They also compared the effects of 8-MOP/UV-A and HAL/blue light on cell killing to evaluate the feasibility of replacing 8-MOP in the current ECP technology with HAL.

The inventors further found that cell proliferation was decreased by HAL/UV-A, HAL/blue light, 8-MOP/UV-A or HAL/8-MOP/UV-A. At sufficient doses, the cells were killed by all the regimens; however, the mode of cell death was dependent on the treatment conditions. 8-MOP/UV-A produced apoptotic death exclusively; whereas both apoptosis and necrosis were induced by HAL/UV-A or HAL/blue light. They thus concluded that 8-MOP can be replaced by HAL to inactivate the Jurkat cells after UVA irradiation via apoptosis and necrosis.

A follow-up ex vivo study in blood samples from GVHD patients demonstrated the superiority of 5-ALA to 8-MOP in ECP-mediated killing of CD4+ and CD8+ cells. These findings indicate an improved efficacy of photopheresis using 5-ALA.

FIGURES

FIG. 1 (referring to Example 1): A) Spectra of HAL-induced PpIX in Jurkat cells. B) Spectra of emitted light by UV-A lamps.

FIG. 2 (referring to Example 1): Photodynamic inactivation of Jurkat cells using HAL.

Figure 3:
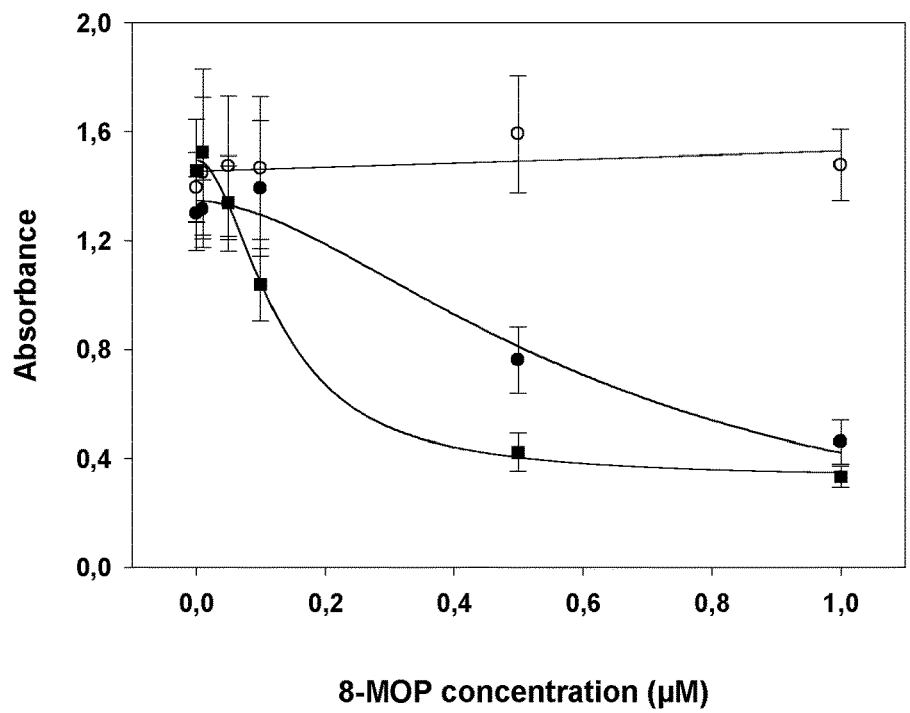

FIG. 3 (referring to Example 1): Photoinactivation of Jurkat cells using 8-MOP.

Figure 4:
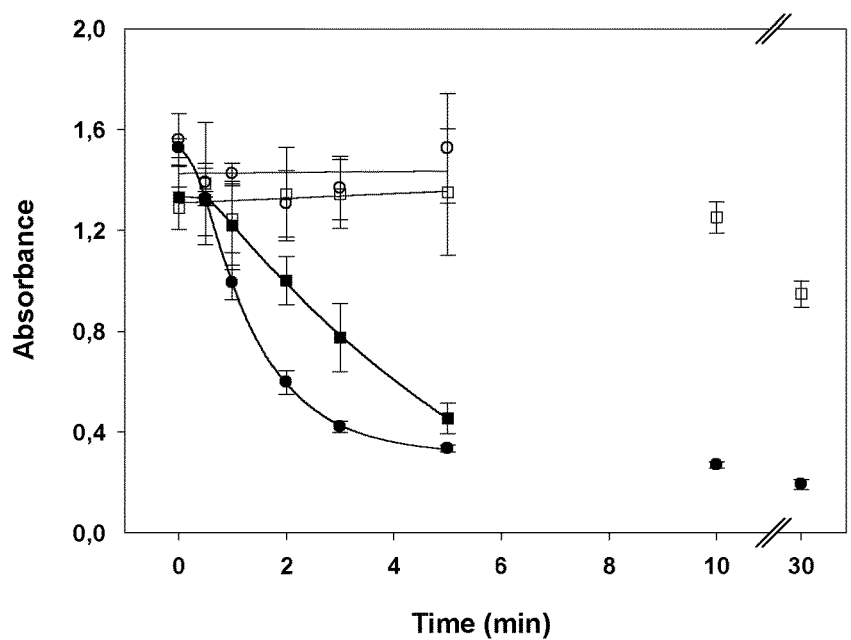

FIG. 4 (referring to Example 1): Dependence of Jurkat cell photoinactivation by 8-MOP on UV-A light source.

Figure 5:
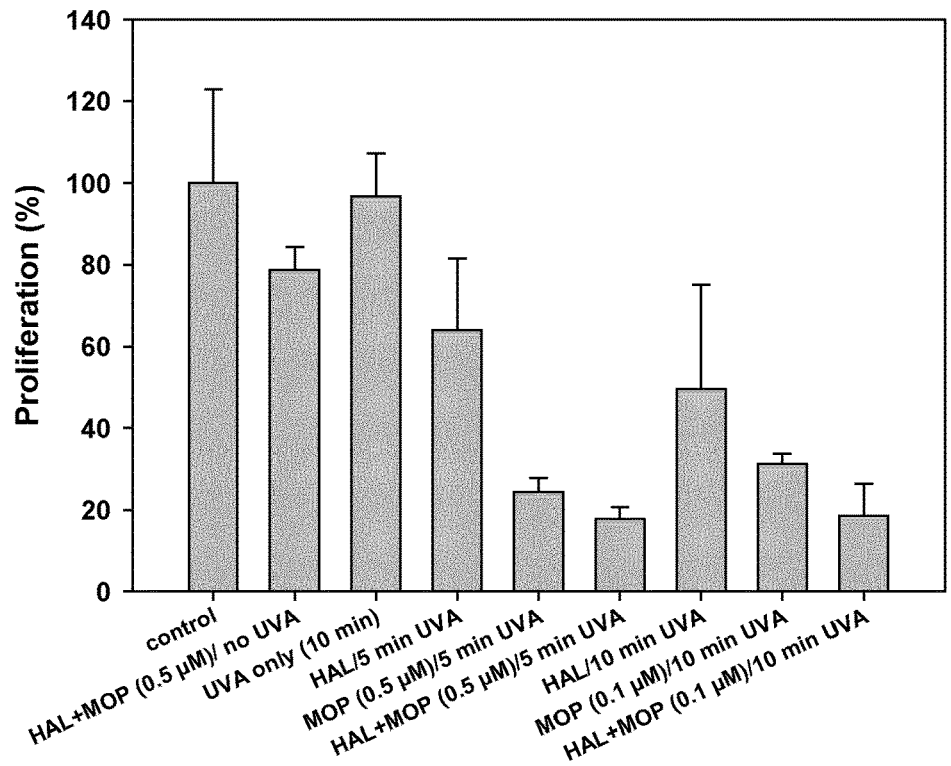

FIG. 5 (referring to Example 1): Photoinactivation of Jurkat cells by using combination of HAL with 8-MOP and irradiation by UV-A light.

Figure 6:
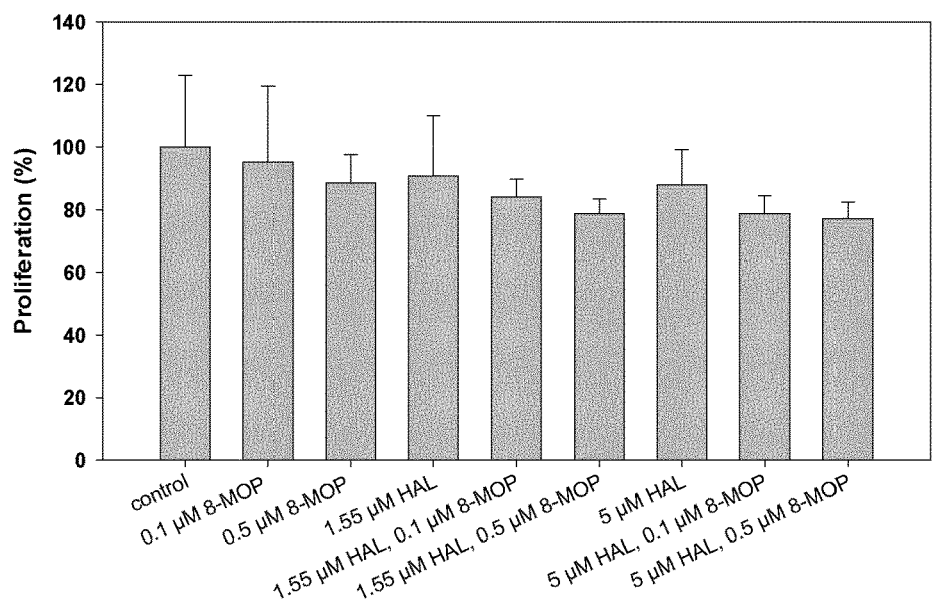

FIG. 6 (referring to Example 1): Dark toxicity (relative to control).

Figure 7:
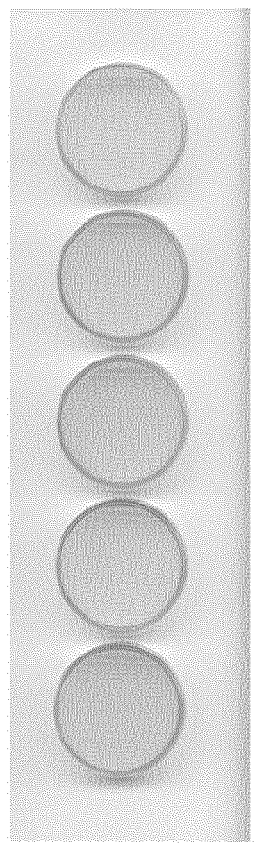

FIG. 7 (referring to Example 1): Cell survival assay.

Figure 8:
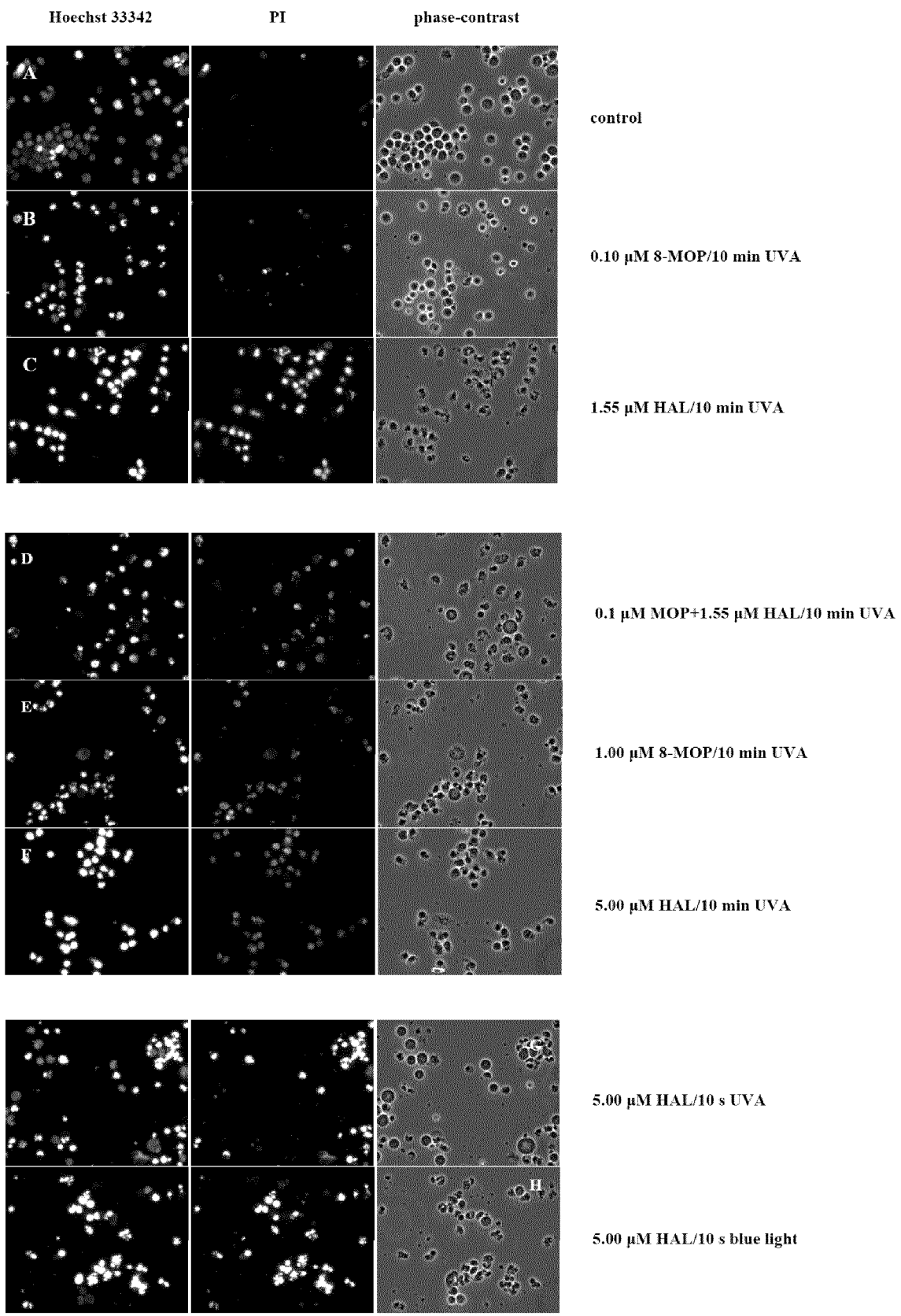

FIG. 8 (referring to Example 1): Fluorescence images of Jurkat cells after different treatments.

Figure 9:
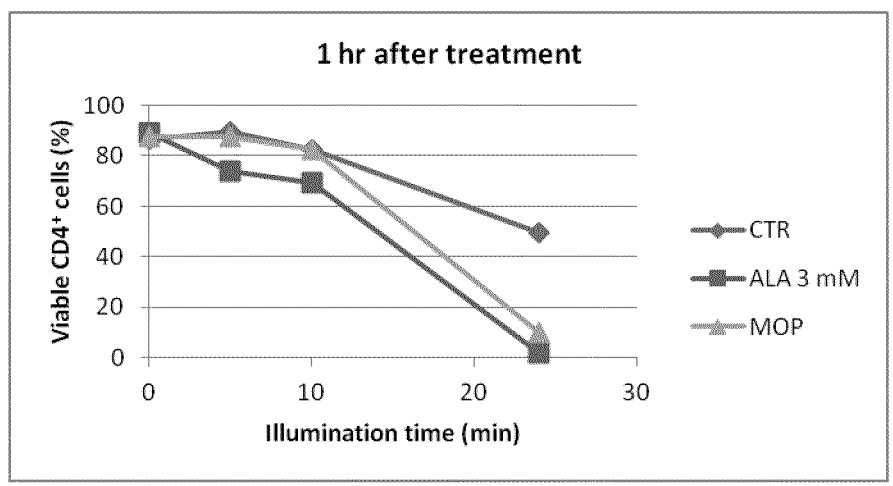
Figure 9:
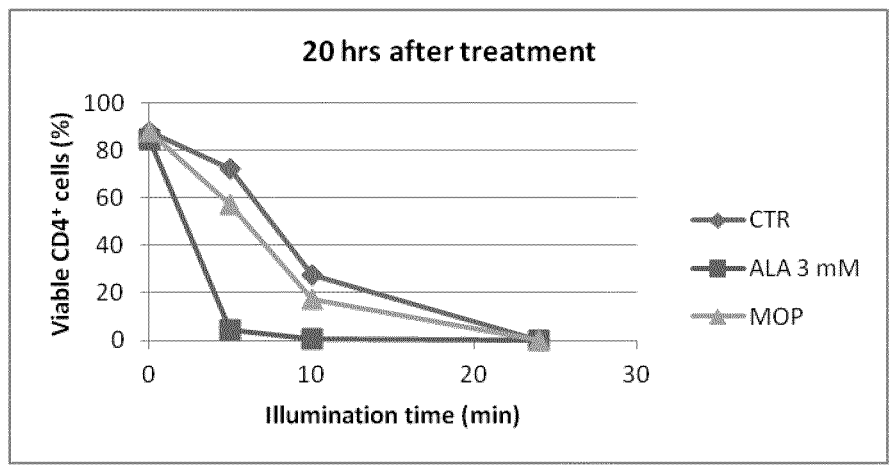

FIG. 9 (referring to Example 2): The effects of 5-ALA on $CD4^+$ T lymphocytes.

Figure 10:
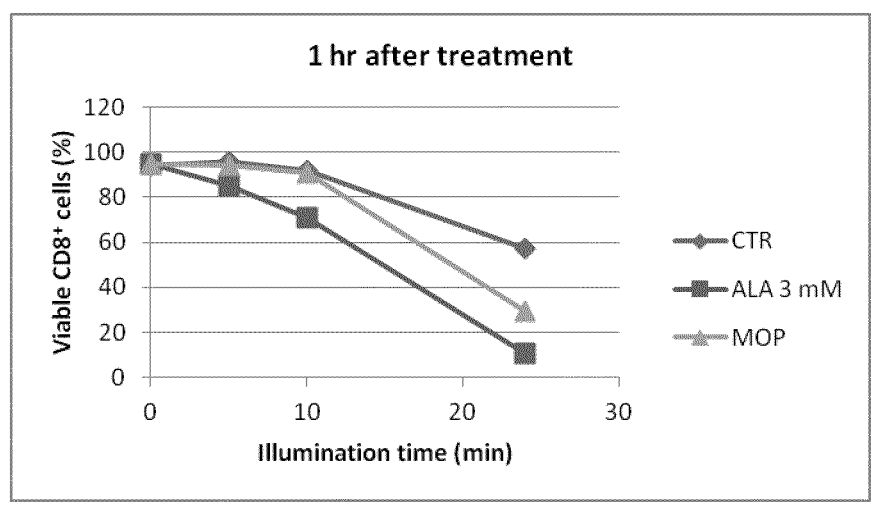
Figure 10:
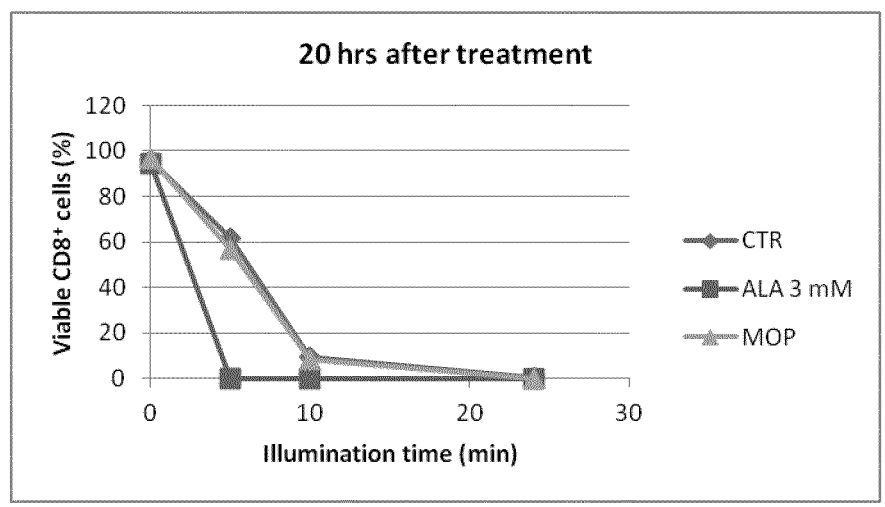

FIG. 10 (referring to Example 2): The effects of 5-ALA on $CD8^+$ T lymphocytes.

Figure 11:
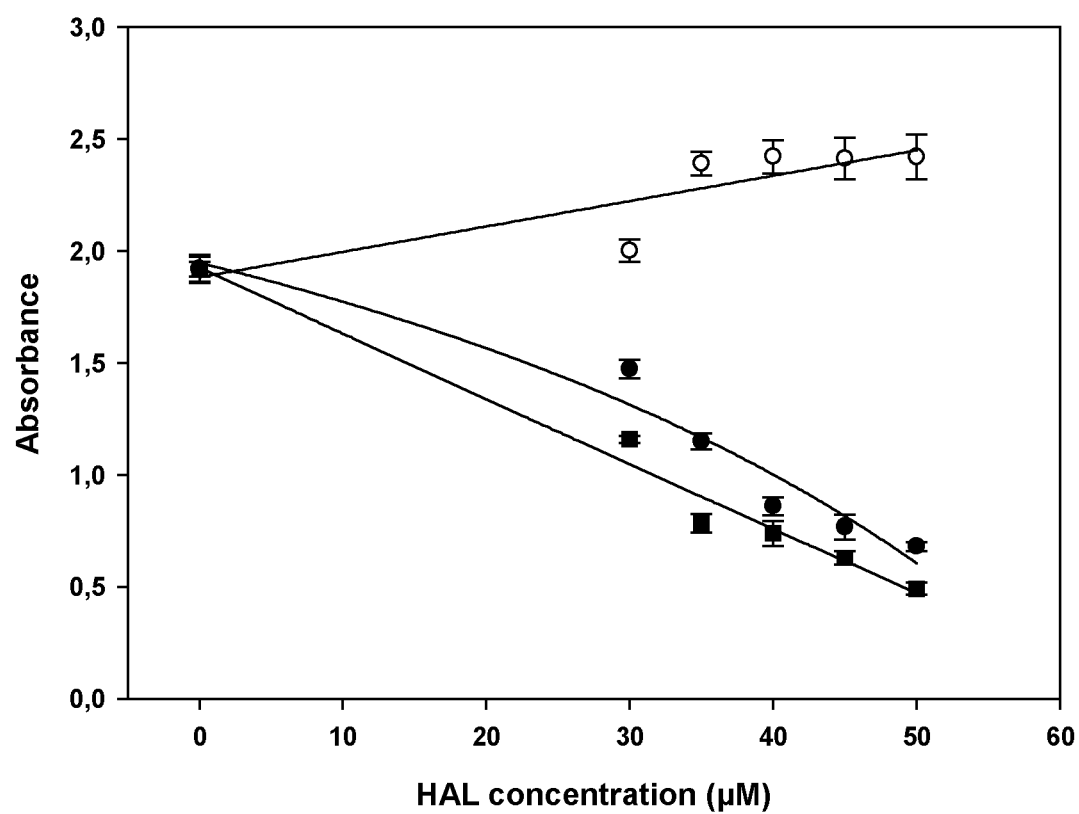

FIG. 11 (referring to Example 3): Photodynamic inactivation of human T-cell lymphoma cell line using HAL.

Figure 12:
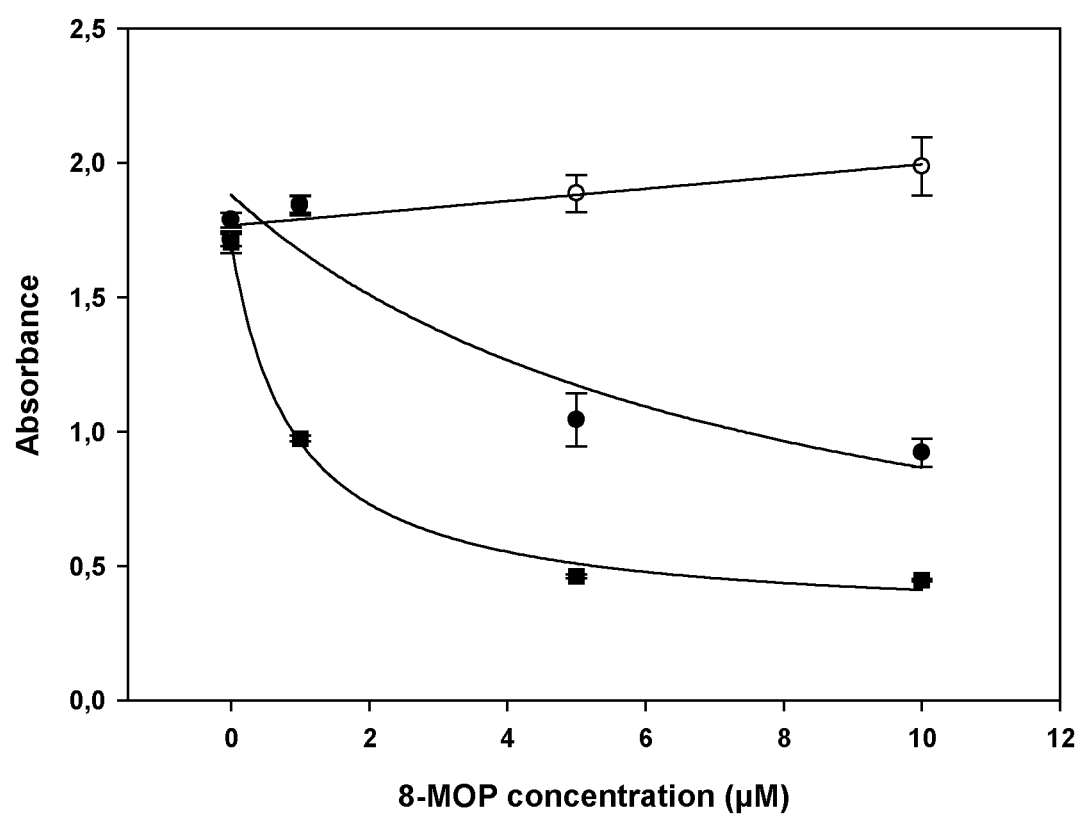

FIG. 12 (referring to Example 3): Photodynamic inactivation of human T-cell lymphoma cell line using 8-MOP.

Figure 13:
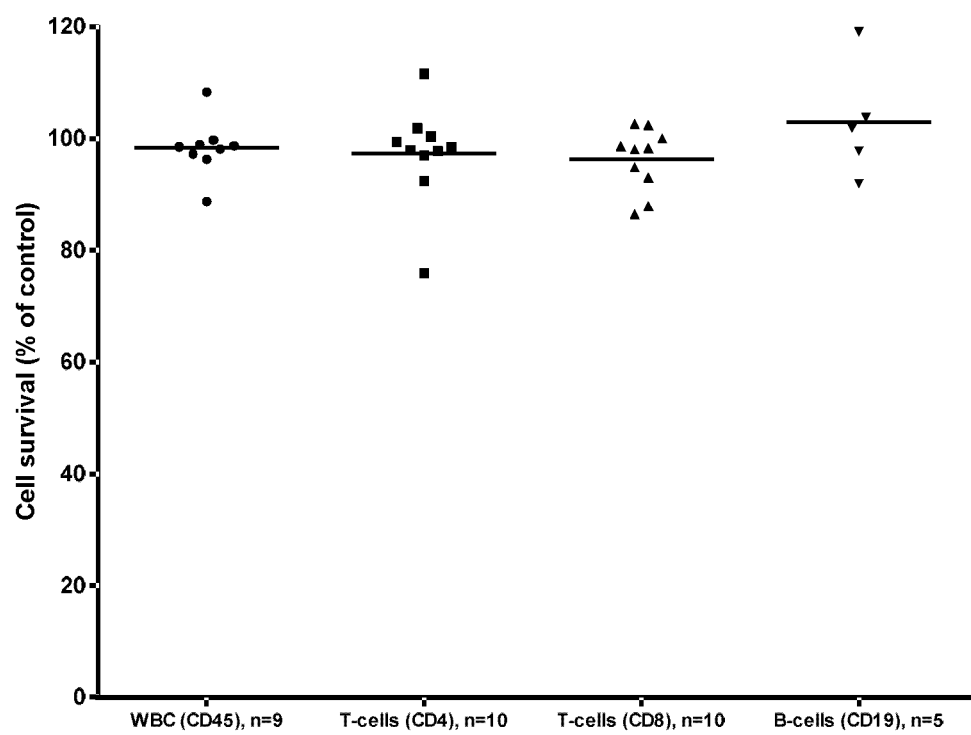

FIG. 13 (referring to Example 4): 5-ALA dark toxicity on human leukocytes Different analysed fractions from the same treated patient blood samples.

FIG. 14 (referring to Example 2): percentages of $CD4^+$/$CD8^+$ T-cell survival at 1 hour and 20 hours after treatment with UVA alone (control), UVA plus 5-ALA or UVA plus 8-MOP. The UVA light dose was 0.158 $J/cm^2$.

EXAMPLE 1

Materials and Methods.
Chemicals.

Hexaminolevulinate (HAL) was provided by Photocure ASA (Oslo, Norway). A fresh stock solution of HAL was prepared in a mixture (1:9) of ethanol and serum free RPM' 1640 medium (PAA Laboratories GmbH, Fisher Scientific, Norway) to a concentration of 8 mM before each experiment. The stock solution of 8-methoxypsoralen (8-MOP) was prepared in absolute ethanol and kept frozen until use. All the chemicals used were of the highest purity commercially available.

Cell Line.

The human T-cell lymphoma cell line, Jurkat (ATCC number: TIB-152™), growing in suspensions at passages 4-24 was used in the study. The cells were incubated in RPMI 1640 medium supplemented with 10% fetal bovine serum (FBS, Gibco, Invitrogen, Norway), L-glutamine (Gibco, Invitrogen, Norway), penicillin and streptomycin (Gibco, Invitrogen, Norway). For subcultivation, the cells were diluted to a density of $3 \times 10^5$ cells/ml every second day. For experiments, the cells were diluted to a density of $1 \times 10^6$ cells/ml day before the start of experiment.

Fluorescence Spectroscopy.

Fluorescence excitation spectra were recorded by means of Perkin Elmer LS50B Luminescence Spectrometer (Norwalk, Conn.) at the emission wavelength of 635 nm. A 15 nm slit width and a $1.0 \times 0.4$ $cm^2$ quartz cuvette were used for the measurements.

The emission spectra of the UV and blue lamps were recorded by using fibre-coupled spectrometers (USB4000, Ocean Optics, Duiven, The Netherlands and Avantes AvaSpec-2048x14-USB2, The Netherlands, respectively).

Photodynamic and Psoralen/UV-A Treatments.

The cells were collected from the cultivation flasks, centrifuged at 1400 rpm for 5 min and diluted in the serum-free RPMI 1640 medium to a density of $37.5 \times 10^5$ cells/ml. Eighty microliters of cell suspension were portioned into 96 well plates. After the addition of 10 μl of HAL solution or serum-free RPMI 1640 medium (controls), the cells were incubated for 4 hours in the darkness at 37° C. Approximately 5 min before the end of incubation with HAL, 10 μl of 8-MOP solution or serum-free RPMI 1640 medium (controls), were added to the wells. After 4 hours incubation with HAL and 5 min incubation with 8-MOP, the samples were irradiated either with UV-A, blue light or both at the exposure times indicated in the Results section.

For the UV-A irradiation of samples, a home-made UV-A lamp (Sorensen UV-A lamp, Phillips Th 20W/09) emitting light mainly in the region 340-410 nm was used (FIG. 1). For the blue light illumination of samples, the light from a bank of four fluorescent tubes (model 3026, Applied Photophysics, London, United Kingdom) emitting light mainly in the region 410-500 nm with a maximum around 440 nm was used (FIG. 1).

In Vitro Cell Proliferation Assay.

Cell proliferation was assessed with a commercially available kit using a colorimetric method based on the cellular conversion of a tetrazolium compound (3-(4,5-dimethylthiazol-2-yl)-5-(3-carboxymethoxyphenyl)-2-(4-sulfophenyl)-2 Htetrazolium, inner salt, MTS) into a formazan product, which can be detected by 492 nm absorbance. Twenty four hours after irradiation, 20 μl of MTS (Promega Corporation, Madison, Wis.) was added to each well. Absorbance at 492 nm was measured after one hour incubation at 37° C. by means of a well plate reader (Multiskan Ex, Labsystems, Finland).

In Vitro Long Term Cell Survival Assay.

Methylcellulose-based medium human MethoCult® with recombinant cytokines, (H4034, StemCell Technologies, France) was used for survival assay. Immediately after treatments, 120 μl of serum-free RPMI 1640 medium containing 200 Jurkat cells were added to 1.2 ml of MethoCult®. The samples were treated according to the manufacturer's instructions and suspensions were transferred into 35 mm Petri dishes. They were incubated at 37° C. in a humidified incubator with 5% $CO_2$.

Assessment of Apoptotic Cells.

Apoptotic cells were identified by fluorescence microscopy based on nuclear morphology after staining with 4.0 μg/ml Hoechst 33342 (Sigma, St. Louis, Mo.) at 37° C. for 10 min. This assay was verified in our previous experiments [7]. The filter combination consisted of a 330 to 380 nm excitation filter, a 400 nm beam splitter, and a 420 nm long-pass emission filter. 2.5 μg/ml of propidium iodide (PI) were also added to the samples to confirm cell death. For PI fluorescence detection, the filter combination consisted of a 540/25 nm excitation filter, a 565 nm beam splitter, and a 605/55 nm band-pass emission filter. Fluorescence images were captured by a highly light sensitive thermo-electrically cooled charge-coupled device camera ORCAII-ER (Hamamatsu, Japan).

Statistical Analysis.

For statistical evaluation of data and curve fittings, Sigma plot software was used. The Student's t-tests were applied for statistical analysis.

Results.

Spectral Measurements.

The fluorescence excitation spectrum of cellular HAL-induced PpIX was measured in the suspension of Jurkat cells incubated with HAL in serum-free medium for 4 hours. The spectra of lights emitted by the lamps used in our laboratory and by the light source of the clinically used Therakos photopheresis system were measured under various settings (compact lamp, fluorescent tubes only, light transmitted through plastic, etc.).

From the comparison of the measured spectra (FIG. 1A) two conclusions can be drawn. First, the emission spectra of all the lamps partially overlap the excitation spectrum of cellular HAL-induced PpIX. Second, the light emitted by UV lamps depends on the settings (FIG. 1B).

Treatment with HAL and Light.

Figure 1B:
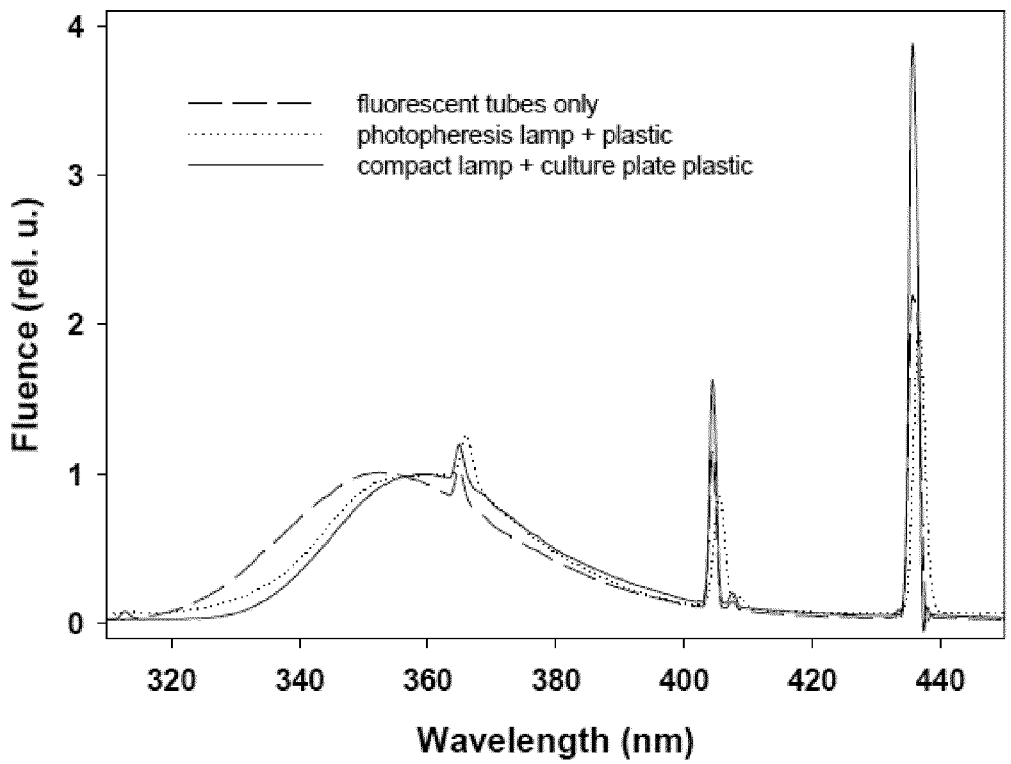
Figure 2A:
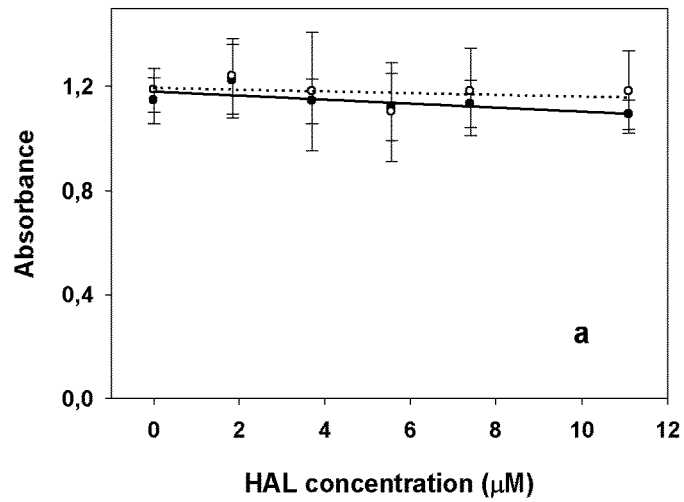
Figure 2A:
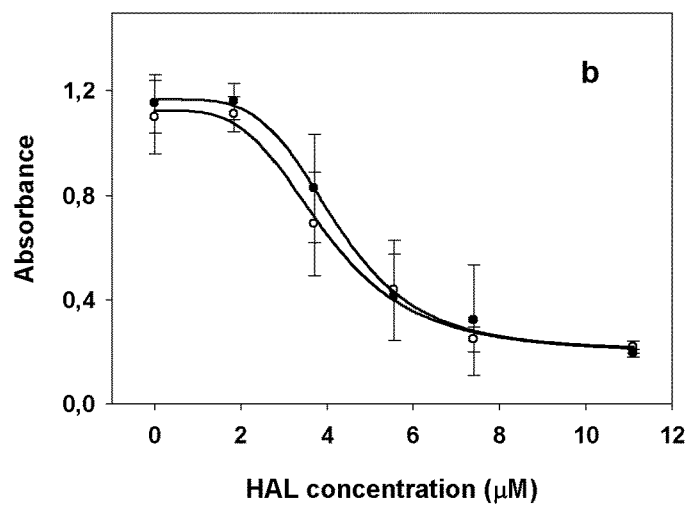
Figure 2A:
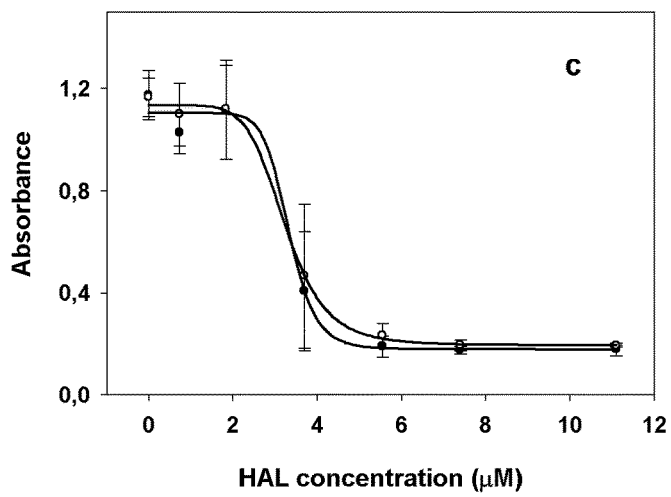
Figure 2B:
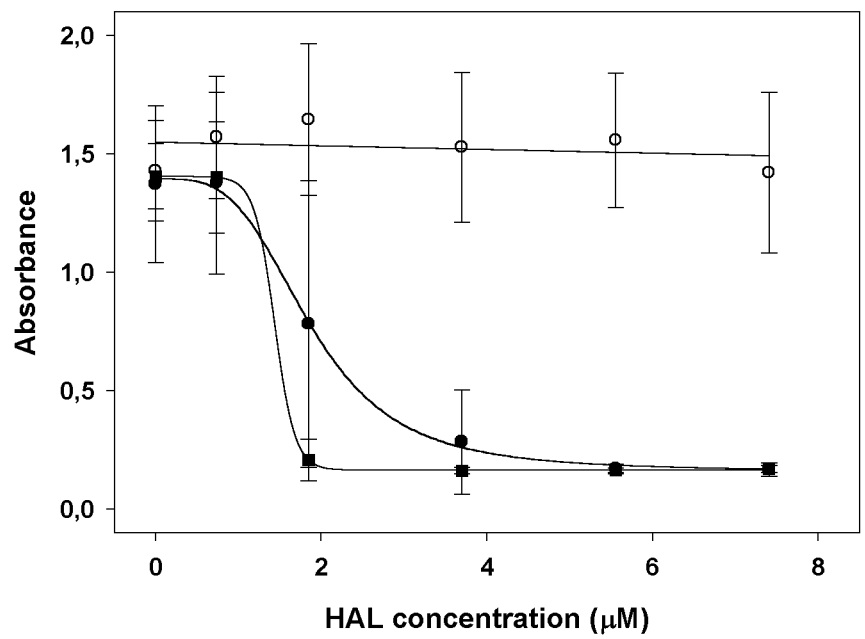
Figure 2C:
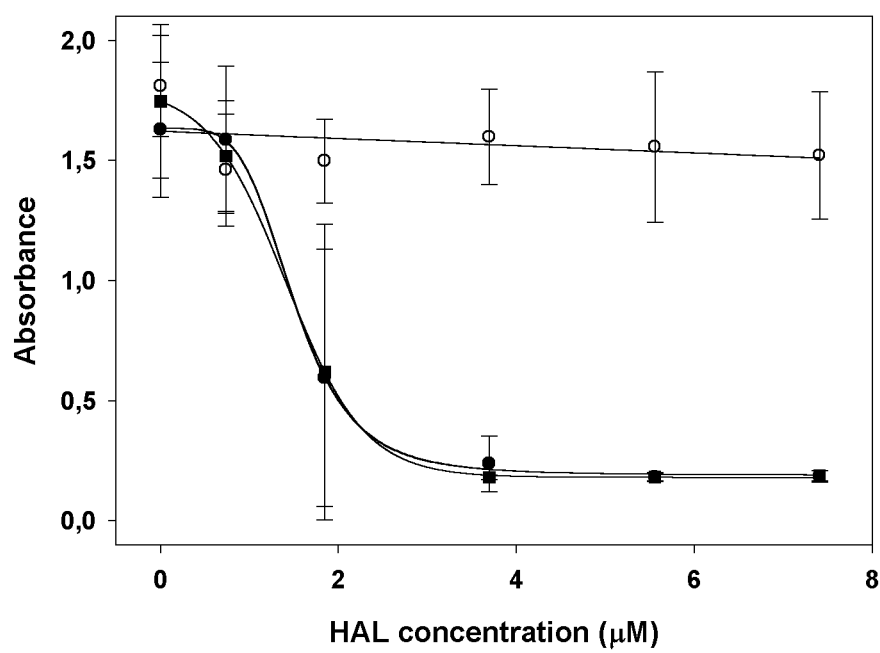

The fluorescence excitation spectrum of HAL-induced PpIX produced in cells has shown a considerable overlap with emission spectra of both blue as well as UV-A lamps used in the present study (FIG. 1A). The sensitivity of Jurkat cells to HAL-mediated PDT was therefore examined after irradiation of the cells by either blue or UV-A light. Ten or 20 s blue light illumination, a high enough dose typically used for photodynamic inactivation of leukemia and lymphoma cell lines; and 5 or 10 min UVA irradiation, corresponding roughly to the time periods of cell exposure to UV-A light during clinical ECP, were tested. Cell proliferation, evaluated by MTS assay, was found to decrease in a concentration-dependent manner in all cases (FIG. 2A). Presence of 1.00 µM 8-MOP in the samples during HAL-based PDT with blue light did not affect cell proliferation. The same results, within experimental error, were obtained when serum (FBS, final concentration of 10%) was added to the cells after UV-A irradiation (FIGS. 2B, C).

These results clearly show that HAL can be used in combination with the Therakos UV-A light to photoinactivate cells.

Treatment with 8-MOP and Light.

The photosensitivity of Jurkat cells to the combined treatment with 8-MOP and UV-A light was first tested in the absence of HAL. At both UV-A irradiation times tested (5 and 10 min), increasing 8-MOP concentration in the samples resulted in decreasing cell proliferation measured by MTS assay (FIG. 3). Since the emission spectrum of the blue lamp occurs far from the action spectrum of 8-MOP (e.g. [38]), activation of 8-MOP by the blue light has not been tested. On the contrary, the effect of 8-MOP is expected to be dependent on the spectral range of the emission spectrum of the UVA lamp. Indeed, the ability of 1.00 µM 8-MOP to sensitise the cells to photoinactivation, was significantly increased when the spectrum of the UV-A lamp was shifted by only few nm (FIG. 4).

The experiments clearly document that the effect of 8-MOP is highly dependent on spectral region covered by the UV-A light.

Treatment with the Combination of HAL, 8-MOP and Light.

Since both HAL and 8-MOP can generate an effect of cell photoinactivation after UVA light irradiation, the possibility of using combination of the two drugs at reduced concentrations was tested. For this purpose several combinations of 8-MOP and HAL were explored (Table 1). A significantly lower cell proliferation could be achieved after the incubation of the cells with 0.10 µM 8-MOP+1.55 µM HAL as compared to corresponding concentrations of 8-MOP or HAL alone if followed by 10 min UV-A irradiation (FIG. 5). Similar effect could be achieved with the combination of 0.50 µM 8-MOP+1.55 µM HAL if followed by 5 min UV-A irradiation (FIG. 5). Qualitatively the same results were obtained when serum (10% FBS) were added to the samples after UV-A irradiation (not shown). A HAL concentration of 5.00 µM was sufficient to decrease cell proliferation to minimum after light exposure, therefore, the effect of combination with 8-MOP could not be tested.

The data thus demonstrate the possibility of cell photoinactivation by the combination of HAL with 8-MOP, each given at concentrations lower than those necessary for the cell photoinactivation alone.

Dark Toxicity.

8-MOP binds to DNA raising concerns about its toxicity. HAL may also be toxic when given systemically. Therefore, in each experiment, samples treated with the drugs but not with the light were included to check for the dark toxicity of the drugs. In general, there was no indication for dark toxicities of HAL (up to 11.00 µM; FIG. 2, 6) or 8-MOP (up to 1.00 µM; FIGS. 3, 4, 6) based on the data of MTS assay. Slightly lower cell proliferation rates were found when combinations of the drugs were used to treat the cells (FIG. 6).

Long Term Cell Survival.

All treatment regimes tested resulted in decreases in Jurkat cell proliferation. To check whether the decrease in cell proliferation correlated with long term cell death, a clonogenic assay in a semisolid medium was intended after the following treatments: 1.0 µM MOP/10 min UV-A, 5.0 µM HAL/10 min UV-A, 0.1 µM MOP+1.55 µM HAL/10 min UV-A, 7.4 µM HAL/10 s blue light. Surprisingly, a week after the cell seeding, in none of the samples (including control, untreated ones) compact colonies could be found, although the colonies were expected to form in such special medium [39-41]. In the control sample, however, numerous living single cells were seen. After two weeks, spread and overlapping areas of high cell densities appeared in control samples, which covered almost the whole area of the dishes. No living cells were seen in the samples treated with UV-A. In some cases, occasional areas of dense cells, similar to those seen in controls, were visible in the samples treated with the combination of HAL with blue light (Table 2). This is in agreement with the results depicted in FIG. 2 showing that at the conditions (7.4 µM HALJ10 s blue light), cell proliferation did not decrease completely. Consistent with the presence of living, metabolizing cells, a yellowish change of the medium colour was noticed in control samples (FIG. 7).

Cell Death Assessment.

All treatments tested in the present study (8-MOP/UV-A, HAL/blue light, HAL/UV-A, MOP+HAL/UV-A) could induce death of Jurkat cells in a drug or light dose-dependent manner. Twenty hours following the treatments, the cells were analyzed by fluorescence microscopy in order to check whether the modes of cell death differ depending on the treatment modality. There were considerable differences in the contents of apoptotic bodies present in the samples. While almost all the cells seemed to die by apoptosis after the treatment with 1.00 µM 8-MOP followed by UV-A, no apoptotic bodies could be seen in the samples treated with 5.00 µM HAL and 10 min UV-A irradiation (FIG. 8). The amount of apoptotic bodies among dead cells in the samples treated with HAL was dependent on the treatment regimen (Table 3).

Discussion

In the present study, the inventors have tested HAL in combination with UV-A to inactivate T-cell lymphoma Jurkat cell line as an in vitro model of cutaneous T-cell lymphoma and compared the effect with those achieved under typically used regimens combining either UV-A irradiation with sensitization of cells with 8-MOP or blue light irradiation with treatment of cells with HAL.

Decrease in both proliferation and survival of Jurkat cells could be induced by the treatment with HAL and UV-A irradiation. This is not surprising due to a partial overlap between excitation spectrum of PpIX and the emission spectrum of UV-A lamp used in this study. The overlap is comparable with that between PpIX excitation spectrum and the emission spectrum of the used blue light lamp (FIG. 1A). The blue light lamp was shown to be effective for inactivation of cells of various origins, including leukemia and lymphoma cell lines after HAL-PDT [7, 8, 34-37]. Decrease in proliferation of Jurkat cells after the treatment with HAL and UV-A light is in agreement with results of another study, where the combination of ALA and UV-A was tested with T-cell lymphoma HUT-78 cell line for the purposes of PUVA treatment [42].

Depending on the treatment regimen used, differences could be seen in the mode of cell death. While only apoptosis was induced when cells were treated with 8-MOP and UV-A light, parameters such as HAL concentration, light source (UV-A or blue light) and irradiation time affected the mode of the death of Jurkat cells in the case of HAL-induced cell photoinactivation.

As discussed in several publications, the therapeutic effect of ECP in vivo is not caused by cell inactivation only, but additionally relies on the induction of immune response (for references see [43]). In this regard, it is important to mention that several publications discussed the significance of the mode of cell death for induction of immune effects [44-48]. It has been recognised that viable cells are able to discriminate apoptotic from necrotic targets via distinct cell surface receptors and such receptors can induce signalling events that differ for apoptotic compared with necrotic targets [49]. Our data show that apoptosis is induced by 8-MOP-UV-A and the clinical experience indicates that this mode of cell death is efficient to achieve a treatment effect of photopheresis. Apoptosis as well as necrosis could be induced by HAL-PDT in the present study and the question is whether appearance of necrotic cells would be beneficial for the treatment outcome. In this respect, immunopotentiation induced by PDT has been documented in numerous publications (reviewed in e.g. [14, 50]). Importantly, vaccines and lysates generated by exogenous photosensitiser-mediated PDT were shown to be more effective than those generated by means of UV and ionizing irradiations or a freeze-thaw technique [51-53]. Improved effect of PDT-generated vaccines has been ascribed to the concurrent appearance of necrotic and apoptotic cells under PDT treatment protocols contrary to the presence of pure apoptotic or pure necrotic cells under UV or ionizing radiation protocols, respectively [51]. It should be mentioned, however, that under certain conditions, PDT was reported to cause immunosuppression as well (for references see [50]).

ECP is a recommended treatment of CTCL and there is fair evidence to support its use in GVHD [1]. However, many patients experience refractory disease, thus further development of the current ECP regime may hopefully be of benefit to patients.

Based on the data of the present study, the inventors concluded that HAL is effective for the photoinactivation of T-cell lymphoma Jurkat cell line after using a UV-A lamp with an emission spectrum similar to that of the light source used in the commercial Therakos photopheresis system. HAL-UV-A induced both apoptosis and necrosis of the Jurkat cells and may thus provide a potential option for enhanced efficacy of ECP. If HAL should be used for ECP, the treatment conditions need to be optimized in subjects with an intact immune system to achieve induction of a desirable immune response.

TABLE 1

Conditions of the cell treatment with the combination of HAL, 8-MOP and UV-A light.

| 8-MOP (µM) | HAL (µM) | UV-A (min) |
|---|---|---|
| 0.10 | 1.55 | 10 |
| 0.10 | 5.00 | 10 |
| 0.50 | 1.55 | 5 |
| 0.50 | 5.00 | 5 |

TABLE 2

Number of high cell density areas formed in semisolid medium 2 weeks after treatment.

| Sample | Number of colonies |
|---|---|
| control (no treatment) | many |
| 1.00 µM MOP/10 min UV-A | 0.8 ± 2.0 (1/6*) |
| 5.00 µM HAL/10 min UV-A | 0 |
| 7.40 µM HAL/10 s blue light | 4.5 ± 5.6 (4/6) |
| 1.55 µM HAL + 0.10 µM MOP/10 min UV-A | 0 |

*number of experiments when colonies were formed/total number of experiments

TABLE 3

Assessment of the mode of cell death after HAL-induced photoinactivation. (Quantitative evaluation was not possible due to the disintegration of apoptotic cells.)

| Drug concentration | Irradiation | Cell appearance 20 hours after treatment |
|---|---|---|
| 1.55 µM HAL | 10 min UV-A | mostly apoptotic + some alive, or mostly necrotic + some apoptotic* |
| 5.00 µM HAL | 10 min UV-A | only necrotic, no apoptotic |
| 5.00 µM HAL | 10 s UV-A | apoptotic + alive (similar proportions) |
| 5.00 µM HAL | 10 s blue light | mostly apoptotic + some alive |
| 1.55 µM HAL + 0.10 µM 8-MOP | 10 min UV-A | almost only apoptotic + few alive |

*sample to sample variations

FIGURE LEGENDS

FIG. 1 A) Normalized fluorescence excitation spectra of HAL-induced PpIX in Jurkat cells and normalized emission spectra of blue and UV-A lamps. B) Spectra of emitted light by UV-A lamps under different settings (compact lamp used in our laboratory covered with plastic culture plate, fluorescent tubes of the lamp used in our laboratory, lamp of the clinically used photopheresis system).

FIG. 2 Photodynamic inactivation of Jurkat cells using HAL. A) blue light illumination in the absence (open circles)

and the presence (full circles) of 1.00 µM 8-MOP; a) control (no blue light), b) 10 s and c) 20 s blue light illumination. B) UV-A light irradiation by light with the spectrum shown in FIG. 1, fluorescent tubes only; (○) control (no irradiation), (●) 5 min, (■) 10 min irradiation, C) same as B) but, FBS added to the samples (final concentration of 10%) after UV-A irradiation. Each data point represents an average ±S.D. from at least 4 different cell samples.

FIG. 3 Photoinactivation of Jurkat cells using 8-MOP and UV-A light irradiation. (○) control (no irradiation), (●) 5 min, (■) 10 min irradiation. The samples were irradiated by the compact lamp with the spectrum shown in FIG. 1. Each data point represents an average ±S.D. from 6 different cell samples.

FIG. 4 Dependence of Jurkat cell photoinactivation by 8-MOP on UV-A light source. The cells were incubated with 1.00 µM 8-MOP and samples were irradiated by lights with spectra shown in FIG. 1, fluorescent tubes only (●) and whole lamp (■); (○, □) controls (no irradiation). Each data point represents an average ±S.D. from 6 different cell samples except from 10 min and 30 min time points, where only 4 and 2 samples, respectively were used.

FIG. 5 Photoinactivation of Jurkat cells by using combination of HAL with 8-MOP and irradiation by UV-A light. The data for 1.55 µM HAL are shown. The samples were irradiated by the fluorescent tubes light with the spectrum shown in FIG. 1. The data are expressed relative to control. The bars represent an average ±S.D. from 8 different cell samples.

FIG. 6 Dark toxicity (relative to control). The cells were treated with indicated drugs and doses, but the samples were not irradiated by light. The bars represent an average ±S.D. from at least 6 different cell samples.

FIG. 7 Cell survival assay. Change in the color of the medium in control sample three weeks after seeding the cells—consistent with the presence of living, metabolizing cells.

FIG. 8 Fluorescence images of Jurkat cells after different treatments showing nuclear morphology after staining with Hoechst 33342 (left column) and PI (middle column). Phase contrast images are shown in the right column. (A) control, (B) 0.10 µM 8-MOP/UV-A, (C) 1.55 µM HAL/UV-A, (D) 0.10 µM 8-MOP+1.55 µM HAL/UV-A, (E) 1.00 µM 8-MOP/UV-A, (F) 5.00 µM HAL/UV-A, (G) 5.00 µM HAL/UV-A, (H) 5.00 µM HAL/blue light. The samples were irradiated for 10 min (B-F) or 10 s (G, H) by lights with the spectra shown in FIG. 1, fluorescent tubes only (FIG. 1B) or blue lamp (FIG. 1A).

EXAMPLE 2

Evaluation of Ex Vivo Efficacy of ALA-ECP in Patients with cGvHD and CTCL.

Optimization of experimental conditions for ALA-ECP was performed in Jurkat cells, varying ALA concentration (1 to 5 mM) and treatment time (1 to 4 hours) in the presence of 10% foetal bovine serum. The cells were then exposed to UVA for 10 min using an UV-A lamp with almost identical emission spectra to those of the UV-A lamp used in the existing commercial Therakos photopheresis system. The cell survival after the ALA/UVA treatment was measured by fluorescence microscopy with propidium iodide (PI) staining.

A suitable dose and incubation time of ALA was used in leukocyte samples collected from ECP patients. The dark toxicity of ALA at the concentration in question was evaluated, followed by the ALA/UVA-mediated killing efficiency before studies on the mechanism of its action (apoptosis/necrosis). The lymphocytes from patients were incubated with ALA under the optimized experimental conditions before exposure to the UVA lamp in the Therakos Photopheresis System at the same light dose as used in the ECP treatment. The cell survival of ALA dark toxicity, ALA/UVA-mediated killing efficiency and apoptosis/necrosis were measured with flow cytometry using combined labelling of $CD4^+$ or $CD8^+$ with Annexin V/PI staining.

The killing effects of 5-ALA (a porphyrin precursor) plus the UVA light irradiation on $CD4^+$/$CD8^+$ T lymphocytes collected from a Graft versus Host Disease (GvHD) patient who went to a standard photopheresis treatment was evaluated. The cells were exposed to ALA+UVA in the standard photopheresis machine, and percentage survival evaluated at various timepoints between 1 h and 20 h. The 8-MOP plus UVA used for the standard photopheresis was also included for comparison. The cell survival was measured with flow cytometry using a combined staining of CD4/CD8 antibody, Annexin-V and eFluor450.

Data for proliferative/activated CD4+ T-cells from one patient are shown in FIG. 1, and for CD8 T-cells in FIG. 2. The results show that the treatment with ALA plus UVA killed the $CD4^+$ and $CD8^+$ T-cells much more effectively than 8-MOP plus UVA, particularly at a low light dose, ie. 5-min light illumination.

The inventors have so far treated the T-cells from 4 patients with cutaneous T-cell lymphoma or GvHD patients, with similar results, summarized in FIG. 14. It is clear that UVA irradiation alone can kill T-cells, suggesting that there is a need to improve this modality with non-toxic visible light source.

FIGURE LEGENDS

FIG. 9. The killing effects of 5-ALA plus the UVA light irradiation on $CD4^+$ T lymphocytes collected from a GvHD patient.

FIG. 10. The killing effects of 5-ALA plus the UVA light irradiation on $CD8^+$ T lymphocytes collected from a GvHD patient.

FIG. 14. The percentages of $CD4^+$/$CD8^+$ T-cell survival at 1 hour and 20 hours after treatment with UVA alone (control), UVA plus 5-ALA or UVA plus 8-MOP. The UVA light dose was 0.158 $J/cm^2$.

EXAMPLE 3

Under the same conditions as said out in Example 1 above, experiments were performed in Karpas 299, another human T-cell lymphoma cell line different from the Jurkat cells used in Example 1 with similar results shown in FIGS. 11 and 12.

FIGURE LEGENDS

FIG. 11 Photodynamic inactivation of human T-cell lymphoma cell line (Karpas 299) using HAL plus UV-A exposure. (○) control (no irradiation), (●) 5 min, (■) 10 min irradiation.

FIG. 12 Photodynamic inactivation of human T-cell lymphoma cell line (Karpas 299) using 8-MOP plus UV-A exposure. (○) control (no irradiation), (●) 10 min, (■) 20 min irradiation.

EXAMPLE 4

Evaluation of 5-ALA Dark Toxicity on Human Leukocytes

The general safety of 5-ALA in absence of light-mediated activation (dark toxicity) was next evaluated. Blood samples from 10 GvHD or CTLC patients were treated with 10 mM 5-ALA at 37° C. in a 5% $CO_2$ humidified incubator overnight (17-24 hours). Buffy coat samples from patients were directly harvested from the Therakos Photopheresis System during the standard photopheresis treatment. The cells incubated with the culture medium containing no 5-ALA were also included as a control in all individuals. The leukocytes were then labelled with antibodies for flow cytometry analysis of various subpopulations. The antibodies used were: CD45 PerCP-Cyanine5.5 for leukocytes, CD4 FITC for T helper cells, CD8 FITC for T cytotoxic cells and CD19 FITC for B-cells. The cells were also labelled with Fixable Viability Dye eFluor 450 for dead cells and Annexin V for apoptotic/dead cells. The different subpopulations of leukocytes were gated out and analyzed for cell viability. The cells that were negative for both the Fixable Viability Dye eFluor 450 and Annexin V were considered as viable cells.

The results are summarized in FIG. 13, showing different analysed fractions from the same treated patient blood samples. Note that for technical reasons, B-cell fractions were obtained from only 5 patient samples, while a whole blood cell (WBC) fraction was missing for one of the patient samples. Generally, no significant dark cytotoxic effect of 5-ALA was noted on the leukocytes studied, at a concentration (10 mM) and exposure time (17-24 hours) of 5-ALA in excess of that expected to be used in a clinical setting. It has to be noted though, that the concentration and exposure time of 5-ALA finally used in a clinical setting will depend on many factors and the specific circumstances of a case and will thus be subject to change.

REFERENCES

[1] Scarisbrick J J, Taylor P, Holtick U, et al. Photopheresis Expert Group. U.K. consensus statement on the use of extracorporeal photopheresis for treatment of cutaneous T-cell lymphoma and chronic graft-versus-host disease. *Br J Dermatol* 2008; 158:659-78.

[2] Edelson R, Berger C, Gasparro F et al. Treatment of cutaneous T cell lymphoma by extracorporeal photochemotherapy. N Engl J Med 1987; 316: 297-303.

[3] Worel N, Leitner G. Clinical results of extracorporeal photopheresis. Tansfus Med Hemother 2012; 39: 254-62.

[4] Gupta A K, Anderson T F. Psoralen photochemotherapy. *J Am Acad Dermatol* 1987; 17:703-34.

[5] Peng Q, Berg K, Moan J, et al. Review: 5-Aminolevulinic acid-based photodynamic therapy: Principle and experimental research. *Photochem Photobiol* 1997a; 65:235-51.

[6] Peng Q, Warloe T, Berg K, et al. Review: 5-Aminolevulinic acid-based photodynamic therapy: Clinical research and future challenges. *Cancer* 1997b; 79:2282-308.

[7] Furre I E, Møller M T, Shahzidi S, et al. Involvement of both caspase-dependent and -independent pathways in apoptotic induction by hexaminolevulinate-mediated photodynamic therapy in human lymphoma cells. *Apoptosis* 2006; 11:2031-42.

[8] Furre I E, Shahzidi S, Luksiene Z, et al. Targeting PBR by hexaminolevulinate-mediated photodynamic therapy induces apoptosis through translocation of apoptosis-inducing factor in human leukemia cells. *Cancer Res* 2005; 65:11051-60.

[9] Gaullier J M, Berg K, Peng Q, et al. The use of esters of 5-aminolevulinic acid to improve photodynamic therapy on cells in culture. *Cancer Res* 1997; 57:1481-6.

[10] Peng Q, Moan J, Warloe T, et al. Build-up of esterified aminolevulinic-acid-derivative-induced porphyrin fluorescence in normal mouse skin. *J Photochem Photobiol B* 1996; 34:95-6.

[11] Rittenhouse-Diakun K, Van Leengoed H, Morgan J, et al. The role of transferrin receptor (CD71) in photodynamic therapy of activated and malignant lymphocytes using the heme precursor delta-aminolevulinic acid (ALA). *Photochem Photobiol* 1995; 61:523-8.

[12] Hryhorenko E A, Rittenhouse-Diakun K, Harvey N S, et al. Characterization of endogenous protoporphyrin IX induced by delta-aminolevulinic acid in resting and activated peripheral blood lymphocytes by four-color flow cytometry. *Photochem Photobiol* 1998; 67:565-72.

[13] Casas A, Perotti C, Fukuda H, del C Battle A M. Photodynamic therapy of activated and resting lymphocytes and its antioxidant adaptive response. *Lasers Med Sci* 2002; 17:42-50.

[14] Castano A, Mroz P, Hamblin M R. Photodynamic therapy and anti-tumor immunity. Nature Reviews *Cancer* 2006; 6:535-45.

[15] Gollnick S O, Brackett C M. Enhancement of anti-tumor immunity by photodynamic therapy. *Immunol Res* 2010; 46:216-26.

[16] Warloe T, Peng Q, Heyerdahl H, et al. Photodynamic therapy with 5-aminolevulinic acid-induced porphyrins and DMSO/EDTA for basal cell carcinoma. *SPIE* 1995; 2371:226-235.

[17] Christensen E, Skoqvoll E, Viset T et al. Photodynamic therapy with 5-aminolaevulinic acid, dimethylsulfoxide and curettage in basal cell carcinoma: a 6-year clinical and histological follow-up. *J Eur Acad Dermatol Venereol* 2009; 23:58-66.

[18] Christensen E Mork C, Skoavoll E. High and sustained efficacy after two sessions of topical 5-aminolaevulinic acid photodynamic therapy for basal cell carcinoma: a prospective, clinical and histological 10-year follow-up study. *Br J Dermatol* 2012; 166:1342-8.

[19] Stummer W, Pichlmeier U, Meinel T, et al. Fluorescence-guided surgery with 5-aminolevulinic acid for resection of malignant glioma: a randomised controlled multicentre phase III trial. *Lancet Oncol* 2006; 7: 392-401

[20] Stummer W, Novotnt A, Stepp H, et al. Fluorescence-guided resection of glioblastoma multiforme by using 5-aminolevulinic acid-induced porphyrins: a prospectie study in 52 consecutive patients. J Neurosurg 2000; 93: 1003-1013.

[21] Panciani P P, Fontanella M, Schatlo B, et al. Fluorescence and image guided resection in high grade glioma. Clin Neurol Neurosurg 2012; 114: 37-41

[22] Piccirillo S G M, Dietz S, Madhu B, et al. Fluorescence-guided surgical sampling of glioblastoma identifies phenotypically distinct tumour-initiating cell populations in the tumour mass and margin. Br J Cancer 2012; 107: 462-8

[23] Gross S A, Wolfsen H C. The role of photodynamic therapy in the esophagus. Gastrointest Endoscopy Clin N Am 2010; 20: 35-53

[24] Dunn J, Lovat L. Photodynamic therapy using 5-aminolevulinic acid for the treatment of dysplasia in Barrett's oesophagus. Expert Opin Pharmacother 2008; 9:851-8

[25] Menon D, Stafinski T, Wu H, et al. Endoscopic treatments for Barrett's esophagus: a systemic review of safety and effectiveness compared to esophagectomy. BMC Gastroenterology 2010; 10:

[26] Ishizuka M, Abe F, Sano Y, et al. Novel development of 5-aminolevulinic acid (ALA) in cancer diagnoses and therapy. Int Immunopharmacol 2011; 11: 358-365

[27] Regula J, Macrobert A J, Gorchein A, et al. Photosensitisation and photodynamic therapy of oesophageal, duodenal, and colorectal tumours using 5-aminolevulinic acid induced protoporphyrin I X: a pilot study. Gut 1995; 36: 67-75

[28] Sylantiev C, Schoenfeld N, Mamet R, et al. Acute neuropathy mimicking porphyria induced by aminolevulinic acid during photodynamic therapy. Muscle Nerve 2005; 31: 390-3

[29] Peng, Q, Evensen J F, Rimington C, et al. A comparison of different photosensitizing dyes with respect to uptake C3H-tumors and tissue of mice. Cancer Lett 1987; 36: 1-10

[30] Peng Q, Moan J, Warloe T, et al. Distribution and photosensitizing efficiency of porphyrins induced by application of exogenous 5-aminolevulinic acid in mice bearing mammary carcinoma. Int J Cancer 1992; 52: 433-43

[31] Warloe T, Peng Q, Moan J, et al. Photochemotherapy of multiple basal cell carcinoma with endogenous porphyrins induced by topical application of 5-aminolevulinic acid. In: Photodynamic therapy and biomedical lasers. Spinelli P, Dal Fante M, Marchesini R, editors. Excerpta Medica, Elsevier Science Publishers B.V., Amsterdam; 1992; pp. 449-53.

[32] Warloe T, Peng, Q, Heyerdahl H, et al. Photodynamic therapy of human tubulo villous adenomas. SPIE 1995; 2325: 425-36

[33] Noodt, B B, Berg K, Stokke T, et al. Apoptosis induced by photodynamic therapy (PDT) with ALA. Br J Cancer 1996; 74: 22-9

[34] Shahzidi S, Stokke T, Soltani H, et al. Induction of apoptosis by hexaminolevulinate-mediated photodynamic therapy in human colon carcinoma cell line 320D M. J Environ Pathol Toxicol Oncol 2006; 25:159-171.

[35] Shahzidi S, Čunderliková B, Więdlocha A, et al. Simultaneously targeting mitochondria and endoplasmic reticulum by photodynamic therapy induces apoptosis in human lymphoma cells. Photochem Photobiol Sci. 2011; 10: 1773-1782.

[36] Čunderliková B, Vasovič V, Sieber F, et al. Hexaminolevulinate-mediated photodynamic purging of leukemia cells from bone marrow. Bone Marrow Transplant 2010; 45:1553-1561.

[37] Čunderliková B, Vasovič V, Sieber F, et al. Hexaminolevulinate-mediated photodynamic purging of marrow grafts with murine breast carcinoma. Bone Marrow Transplant 2011; 46: 1118-1127.

[38] Ortel B, Gange R W. An action spectrum for the elicitation of erythema in skin persistently sensistized by photobound 8-methoxypsoralen. *J Invest Dermatol* 1990; 94:781-5.

[39] Galietta A, Gunby R H, Redaelli S, et al. NPM/ALK binds and phosphorylates the RNA/DNA-binding protein PSF in anaplastic large-cell lymphoma. *Blood* 2007; 110: 2600-9.

[40] Fakler M, Loeder S, Vogler M, et al. Small molecule XIAP inhibitors cooperate with TRAIL to induce apoptosis in childhood acute leukemia cells and overcome Bcl-2-mediated resistance. *Blood* 2009; 113:1710-22.

[41] Nahimana A, Attinger A, Aubry D, et al. The NAD biosynthesis inhibitor AP0866 has potent antitumor activity against hematologic malignancies. *Blood* 2009; 113: 3276-86.

[42] Akita Y, Watanabe D, Yanagishita T, et al. The effect of psoralen plus ultraviolet A in vitro in HUT-78 enhances by 5-aminolevulinic acid. *Photodermatol Photoimmunol Photomed* 2007; 23:95-7.

[43] Broady R, Yu J, Levings M K. Pro-tolerogenic effects of photodynamic therapy with TH9402 on dendritic cells. *J Clin Apheresis* 2008; 23:82-91.

[44] Melcher A, Gough M, Todryk S, Vile R. Apoptosis or necrosis for tumor immunotherapy: what's in a name? *J Mol Med* 1999; 77:824-33.

[45] Cocco R E, Ucker D S. Distinct modes of macrophage recognition for apoptotic and necrotic cells are not specified exclusively by phosphatidylserine exposure. *Mol Biol Cell* 2001; 12:919-30.

[46] Scheffer S R, Nave H, Korangy F, et al. Apoptotic, but not necrotic, tumor cell vaccines induce a potent immune response in vivo. *Int J Cancer* 2003; 103:105-11

[47] Basu S, Binder R J, Suto R, et al. Necrotic but not apoptotic cell death releases heat shock proteins, which deliver a partial maturation signal to dendritic cells and activate the NF-kB pathway. *Int Immunol* 2000; 12:1539-46.

[48] Srivastava P K. Hypothesis: controlled necrosis as a tool for immunotherapy of human cancer. *Cancer Immun* 2003; 3:4.

[49] Patel V A, Lee D J, Longacre-Antoni A, et al. Apoptotic and necrotic cells as sentinels of local tissue stress and inflammation: Response pathways initiated in nearby viable cells. *Autoimmunity* 2009; 42:317-21.

[50] Chen W R, Huang Z, Korbelik M, et al. Photoimmunotherapy for cancer treatment. *J Environ Pathol Toxicol Oncol* 2006; 25:281-91.

[51] Gollnick S, Vaughan L, Henderson B W. Generation of effective antitumor vaccines using photodynamic therapy. *Cancer Res* 2002; 62:1604-8.

[52] Bae S-M, Kim Y-W, Kwak S-Y, et al. Photodynamic therapy-generated tumor cell lysates with CpG-oligodeoxynucleotide enhance immunotherapy efficacy in human papillomavirus 16 (E6/E7) immortalized tumor cells. *Cancer Sci* 2007; 98:747-52.

[53] Korbelik M, Sun J. Photodynamic therapy-generated vaccine for cancer therapy. *Cancer Immunol Immunother* 2006; 55:900-9.

The invention claimed is:

1. A method of extracorporeal photophoresis treatment of a patient's blood or part of said blood, the method comprising:
    contacting the patient's blood or part thereof with a 5-aminolevulinic acid so as to provide a concentration of 5-aminolevulinic acid between 1 and 10 mM in the blood or part thereof; and
    exposing the resulting blood or part thereof to light of a wavelength between 315 nm and 450 nm inclusive,
    wherein said patient is suffering from a cancer, a lymphocyte-mediated malignant or non-malignant disorder, a T-Cell-mediated disease, an autoimmune disease or is afflicted with a malignancy or has an immunological disease.

2. The method of claim 1,
    wherein the time between contacting said patient's blood or part thereof with said 5-aminolevulinic acid and the exposure to light of said wavelength is between 5 min and 480 min inclusive.

3. The method of claim 1, further comprising: contacting the blood or part thereof with a psoralen.

4. The method of claim 1,
wherein the wavelength of the light is between 380 nm and 450 nm inclusive.

5. The method of claim 1,
patient suffering from a cancer selected from the group consisting of:
T-cell lymphoma, cutaneous T-cell lymphoma, erythrodermic cutaneous T-cell lymphoma;
a haematological cancer, or a lymphocyte leukaemia.

6. The method of claim 1,
wherein said patient is suffering from
a graft versus host disease;
a transplant rejection;
an organ allograft rejection; or
multiple sclerosis, systemic sclerosis, progressive systemic sclerosis (PSS), systemic lupus erythematosus (SLE), rheumatoid arthritis, juvenile onset diabetes mellitus, or type I diabetes mellitus.

7. The method of claim 1,
wherein the part of the patient's blood or part thereof exposed is selected from isolated white blood cells, leukocyte enriched blood, or leukocyte enriched buffy coat having a hematocrit value of 0% to 10% and/or having 5% to 25% of the total peripheryl blood mononuclear cell component.

8. The method of claim 1,
wherein said treatment is performed at an interval of once on two consecutive days per week, or once on two consecutive days per four weeks, or two consecutive days every two weeks; and
wherein said treatment is continued over a period of between 1 and 12 months.

9. The method of claim 1, wherein
the concentration of 5-aminolevulinic acid (ALA),
in said patient's blood or part thereof is between 0.1 and 10 mM or between 0.1 and 10 mg/kg body weight of the subject,
in the absence of serum or in the presence of 5 to 20% serum;
wherein the time between contacting said patient's blood or part thereof is with ALA and the exposure to light is between 30 min and 120 min,
the wavelength of the light is between 315 nm and 1000 nm inclusive and
the dose of light is between 0.01 and 20 J/cm$^2$ inclusive.

10. A method of extracorporeal photophoresis treatment of a patient's blood or part of said blood, the method comprising:
contacting the patient's blood or part thereof with a 5-aminolevulinic acid so as to provide a concentration of 5-aminolevulinic acid between 1 and 10 mM in the blood or part thereof; and
exposing the resulting blood or part thereof to light of a wavelength between 315 nm and 450 nm inclusive,
wherein said patient is suffering from graft versus host disease (GVHD), chronic graft versus host disease (cGvHD) following bone marrow transplantation, chronic graft versus host disease (cGvHD) with cutaneous/mucous membrane involvement, chronic graft versus host disease (cGvHD) with hepatic involvement, and/or acute or chronic graft versus host disease with gastrointestinal/pulmonary involvement.

11. The method of claim 1,
wherein the time between contacting said patient's blood or part thereof with said 5-aminolevulinic acid and the exposure to light of said wavelength is between 15 min and 240 min inclusive.

12. The method of claim 11,
wherein the time between contacting said patient's blood or part thereof with said 5-aminolevulinic acid and the exposure to light of said wavelength is between 30 min and 120 min inclusive.

13. The method of claim 11,
wherein the time between contacting said patient's blood or part thereof with said 5-aminolevulinic acid and the exposure to light of said wavelength is between 45 min and 75 min inclusive.

* * * * *